(12) United States Patent
Cundiff et al.

(10) Patent No.: US 11,376,017 B2
(45) Date of Patent: *Jul. 5, 2022

(54) SURGICAL INSTRUMENTS INCLUDING A SET OF CUTTING BURRS FOR PERFORMING AN OSTEOTOMY

(71) Applicant: Fusion Orthopedics, LLC, Mesa, AZ (US)

(72) Inventors: Adam J. Cundiff, Gilbert, AZ (US); Nathan G. Peterson, Gilbert, AZ (US)

(*) Notice: Subject to any disclaimer, the term of this patent is extended or adjusted under 35 U.S.C. 154(b) by 446 days.

This patent is subject to a terminal disclaimer.

(21) Appl. No.: 16/459,545

(22) Filed: Jul. 1, 2019

(65) Prior Publication Data

US 2021/0000483 A1 Jan. 7, 2021

(51) Int. Cl.
| | | |
|---|---|---|
| A61B 17/14 | (2006.01) | |
| A61B 17/15 | (2006.01) | |
| A61B 17/80 | (2006.01) | |
| A61B 90/00 | (2016.01) | |
| A61B 17/16 | (2006.01) | |
| A61B 17/56 | (2006.01) | |

(52) U.S. Cl.
CPC .......... *A61B 17/151* (2013.01); *A61B 17/142* (2016.11); *A61B 17/1659* (2013.01); *A61B 17/8095* (2013.01); *A61B 90/06* (2016.02); *A61B 2017/568* (2013.01); *A61B 2090/067* (2016.02)

(58) Field of Classification Search
CPC ... A61B 17/1659; A61B 17/142; A61B 17/14; A61B 17/8095; A61B 17/144; B27B 19/006; B23D 61/021
See application file for complete search history.

(56) References Cited

U.S. PATENT DOCUMENTS

| | | | | |
|---|---|---|---|---|
| 2,216,788 | A * | 10/1940 | Severson | B23B 27/16 407/41 |
| 2,658,258 | A * | 11/1953 | Hawkinson | B23D 71/025 407/29.11 |
| 4,625,725 | A * | 12/1986 | Davison | A61B 17/1659 407/29.1 |
| 4,872,452 | A * | 10/1989 | Alexson | A61B 17/1659 606/85 |
| 5,147,364 | A * | 9/1992 | Comparetto | A61B 17/15 606/85 |
| 5,342,365 | A * | 8/1994 | Waldman | A61B 17/1659 407/29.1 |

(Continued)

*Primary Examiner* — David W Bates

(57) ABSTRACT

Surgical instruments for performing osteotomies and particularly, wedge-shaped osteotomies, are disclosed herein. A surgical instrument includes a body with a distal end, a proximal end, a bottom surface, and a top surface including a slope extending upward and along a single plane from the distal end to the proximal end. The surgical instrument further includes multiple cutting burrs positioned on the top surface extending along the slope from the distal end to the proximal end and teeth positioned on the distal end. Further, the body tapers from the distal end to the proximal end. Other surgical instruments include a non-patterned set of cutting burrs along the slope from the distal end to the proximal end or the cutting burrs positioned in multiple rows or columns on the top surface along the slope from the distal end to the proximal end.

20 Claims, 15 Drawing Sheets

(56) References Cited

U.S. PATENT DOCUMENTS

| | | | | |
|---|---|---|---|---|
| 6,083,228 | A * | 7/2000 | Michelson | A61B 17/1671 |
| | | | | 606/79 |
| 6,468,080 | B1 * | 10/2002 | Fischer | A61C 5/88 |
| | | | | 433/149 |
| 8,939,981 | B1 * | 1/2015 | Anderson | A61B 17/141 |
| | | | | 606/82 |
| 9,044,842 | B2 * | 6/2015 | Kang | B24B 37/26 |
| 2003/0032971 | A1 * | 2/2003 | Hausmann | B23D 61/006 |
| | | | | 606/176 |
| 2004/0098000 | A1 * | 5/2004 | Kleinwaechter | B23D 61/006 |
| | | | | D24/146 |
| 2010/0121153 | A1 * | 5/2010 | To | A61B 17/3417 |
| | | | | 600/214 |
| 2010/0145343 | A1 * | 6/2010 | Johnson | A61B 17/1624 |
| | | | | 606/85 |
| 2011/0071527 | A1 * | 3/2011 | Nelson | A61B 17/1624 |
| | | | | 606/85 |
| 2012/0255417 | A1 * | 10/2012 | Frueh | B23D 61/006 |
| | | | | 83/835 |
| 2013/0304070 | A1 * | 11/2013 | Nelson | A61B 18/148 |
| | | | | 606/85 |
| 2019/0314040 | A1 * | 10/2019 | Greenhalgh | A61B 17/1633 |
| 2021/0000486 | A1 * | 1/2021 | Cundiff | A61B 17/142 |
| 2021/0000487 | A1 * | 1/2021 | Cundiff | A61B 17/142 |
| 2021/0071432 | A1 * | 3/2021 | Bordin | E04F 21/1877 |

\* cited by examiner

SURGICAL INSTRUMENTS INCLUDING A SET OF CUTTING BURRS FOR PERFORMING AN OSTEOTOMY

FIELD OF THE TECHNOLOGY

The present technology relates generally to surgical cutting apparatus, and more particularly to, surgical instruments for performing osteotomies.

BACKGROUND

Surgical cutting instruments come in many shapes and sizes. Generally, osteotomy surgical instruments are designed to make straight cuts. In some situations, particularly when a wedge-shaped osteotomy is desired, the user (e.g., a physician, surgeon, etc.) is required to perform multiple osteotomies, cuts, and/or passes to achieve the desired shape. Further, multiple osteotomies with using a surgical instrument that make straight cuts can result in inconsistencies in shape and/or size of the resulting osteotomy wedges in different patients. In other words, it takes more time to perform a wedge-shaped osteotomy than is otherwise needed and/or there is a degree of inconsistency and/or inaccuracy when a traditional surgical instrument is utilized to perform a wedge-shaped osteotomy.

SUMMARY

Various embodiments provide a surgical instrument for performing a surgical osteotomy. One surgical instrument includes a body including a distal end, a proximal end, a bottom surface, and a top surface including a slope extending upward and along a single plane from the distal end to the proximal end. The surgical instrument further includes a plurality of cutting burrs positioned on the top surface and extending along at least a portion of the slope from the distal end to the proximal end and a set of teeth positioned along a radius on the distal end. In some embodiments, the proximal end includes a first horizontal width that is greater than a second horizontal width for the distal end such that the body tapers from the distal end to the proximal end.

Another surgical instrument includes a body including a distal end, a proximal end, a bottom surface, and a top surface including a slope extending upward and along a single plane from the distal end to the proximal end. The surgical instrument further includes a plurality of rows of cutting burrs positioned on the top surface and extending along at least a portion of the slope from the distal end to the proximal end and a set of teeth positioned along a radius on the distal end. In some embodiments, the proximal end includes a first horizontal width that is greater than a second horizontal width for the distal end such that the body tapers from the distal end to the proximal end.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

Figure 1A:
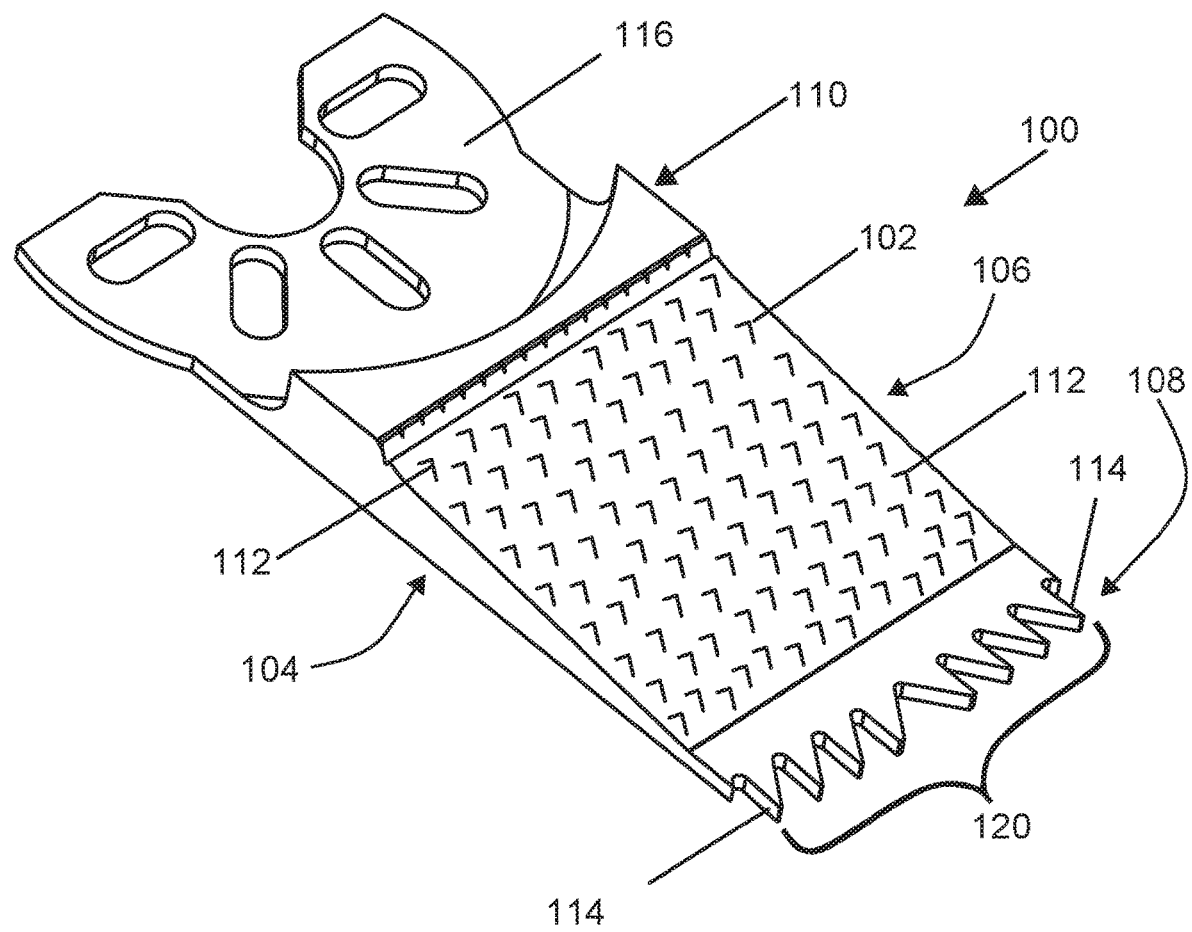
FIG. 1A is a schematic diagram illustrating an overall view of an embodiment of a surgical instrument.
Figure 1B:
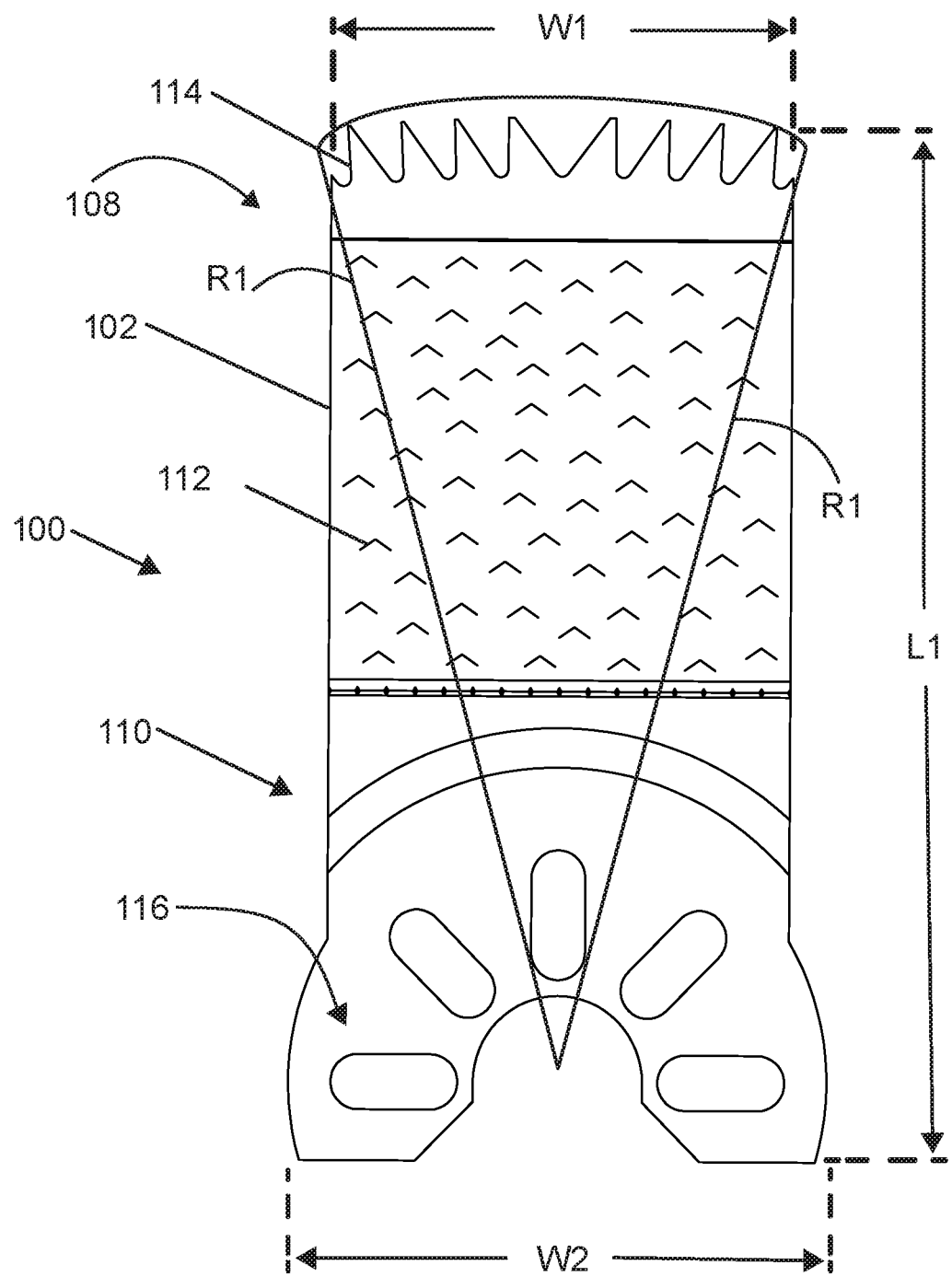
FIG. 1B is a schematic diagram illustrating a top view of the embodiment of a surgical instrument including cutting burrs on the top surface.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present technology may include any type of surgical instrument and is not limited to the style of surgical instrument depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 1E are schematic diagrams illustrating various views of one embodiment of a surgical instrument 100. In various embodiments, the surgical instrument 100 can be utilized to perform a wedge-shaped osteotomy. Further, the wedge-shaped osteotomy can be achieved with a single cut or pass utilizing the surgical instrument 100.

A surgical instrument 100 may be constructed of any suitable material that can cut bone. In various embodiments, the surgical instrument 100 is constructed of a sterilized suitable material that can cut bone. In some embodiments, the surgical instrument 100 includes stainless steel, among other suitable materials and combinations of materials that are possible and contemplated herein. In additional or alternative embodiments, the surgical instrument 100 includes surgical grade stainless steel, among other suitable surgical grade materials and combinations of materials that are possible and contemplated herein.

At least in the illustrated embodiment, the surgical instrument 100 includes, among other features, a body 102 including at least a bottom surface 104, a top surface 106, a distal end 108, and a proximal end 110, a set of cutting burrs 112 positioned on the body 102, a set of cutting teeth 114 positioned on the distal end 108, and an attachment mechanism 116 positioned on the proximal end 110. A body 102 may include any suitable dimensions that can perform an osteotomy. The dimensions may include any suitable dimensions that are capable of performing an osteotomy on a human.

In various embodiments, the body 102 includes a length L1 (see FIG. 1B) in the range of about 15 mm to about 70 mm, among other ranges of length and/or lengths that are possible and contemplated herein. In some embodiments, the body 102 includes a length L1 of about 20 mm, among other lengths that are possible and contemplated herein.

The body 102 further includes a width W1 (see FIG. 1B) at the distal end 108 and a width W2 (see FIG. 1B) at the proximal end 110. In various embodiments, the width W1 is in the range of about 5 mm to about 30 mm, among other ranges of widths and/or widths that are possible and contemplated herein. In some embodiments, the width W1 is about 7.5 mm, among other widths that are possible and contemplated herein. In additional or alternative embodiments, the width W2 is in the range of about 5 mm to about 70 mm, among other ranges of widths and/or widths that are possible and contemplated herein. In some embodiments, the width W2 is about 11 mm, among other widths that are possible and contemplated herein.

In some embodiments, the width W1 and the width W2 are the same width or substantially the same width. In other embodiments, the width W2 is greater than the width W1 such that the proximate end 110 is wider than the distal end 108 or, alternatively, the distal end 108 is narrower than the proximate end 110 (e.g., the width W1 is less than the width W2). That is, in various embodiments, the surgical instrument 100 includes a tapered shape and/or tapers from the distal end 108 to the proximate end 110.

A bottom surface 104 may include any suitable shape and/or profile that can facilitate or assist the surgical instrument 100 in performing an osteotomy (e.g., a wedge-shaped osteotomy). In various embodiments, the bottom surface 104 includes a flat or substantially flat surface, among other profiles and/or planes that are possible and contemplated herein.

A top surface 106 may include any suitable profile upon which a set of cutting burrs 112 can be positioned. In various embodiments, the top surface 106 includes a slope 118 (see FIGS. 1C, 1D, and 1E) that extends upward and/or away from the bottom surface 104 and the distal end 108. The slope 118 may include any suitable grade (e.g., rise over run) that can facilitate and/or assist the surgical instrument 100 in performing an osteotomy and particularly, a wedge-shaped osteotomy. That is, the top surface 106 and/or surgical instrument 100 may include any suitable grade that can facilitate and/or assist the surgical instrument 100 in performing a wedge-shaped osteotomy in one cut and/or one pass.

Figure 1C:
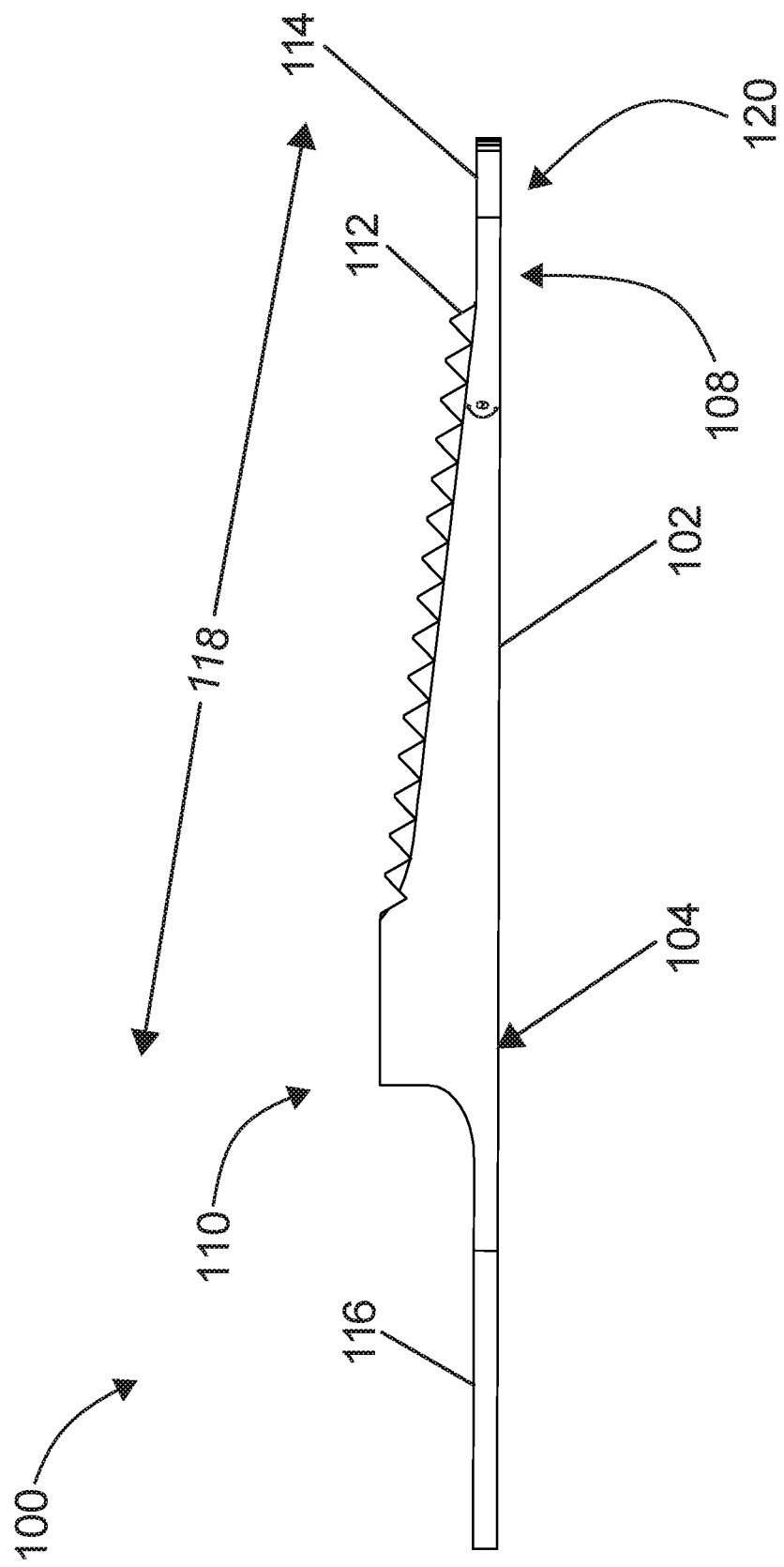
FIG. 1C is a schematic diagram illustrating a side view of the embodiment of a surgical instrument including cutting burrs with the same height.
Figure 1D:
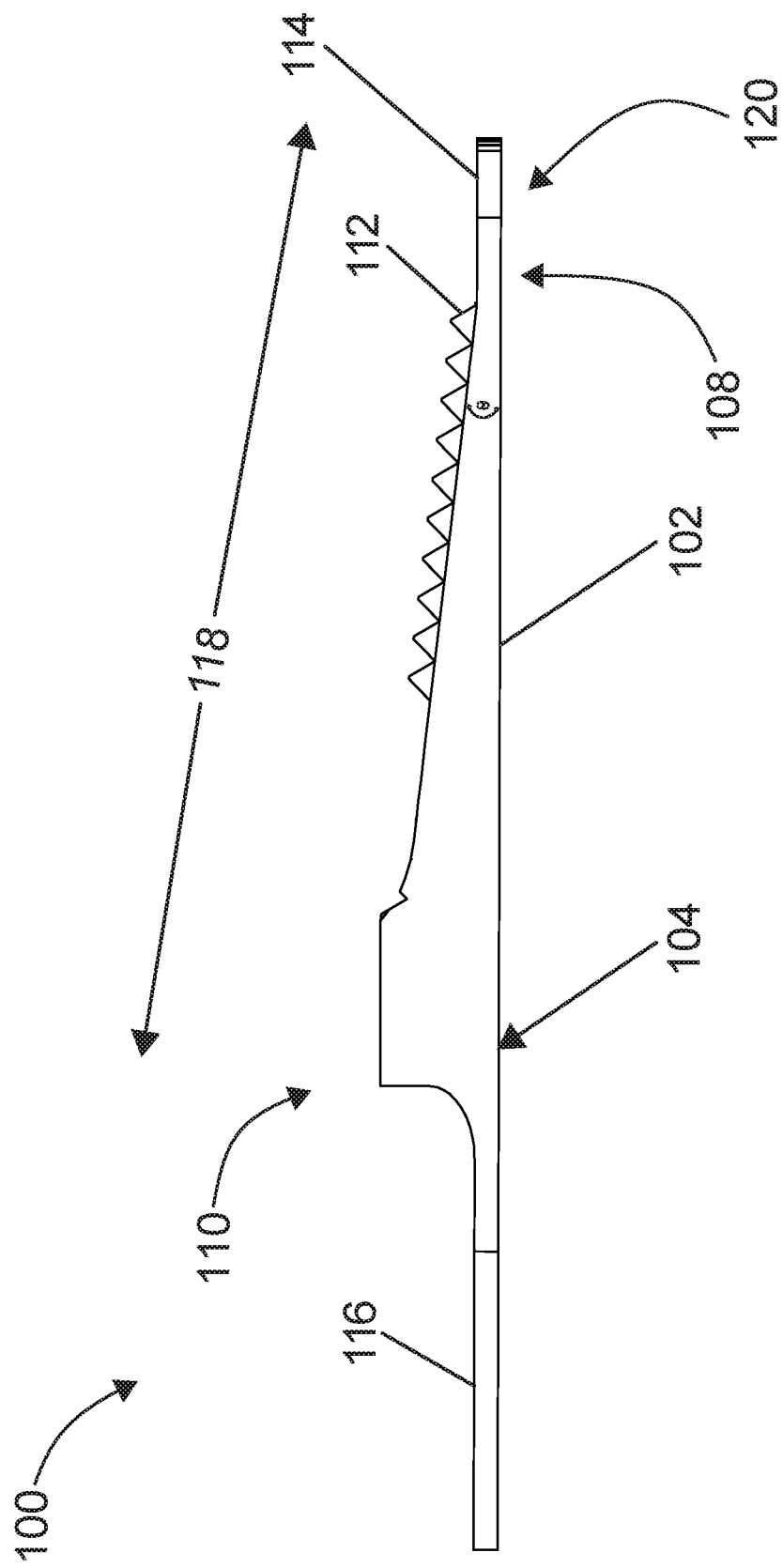
FIG. 1D is a schematic diagram illustrating another top view of the embodiment of a surgical instrument including cutting burrs on a portion of the top surface.
Figure 1E:
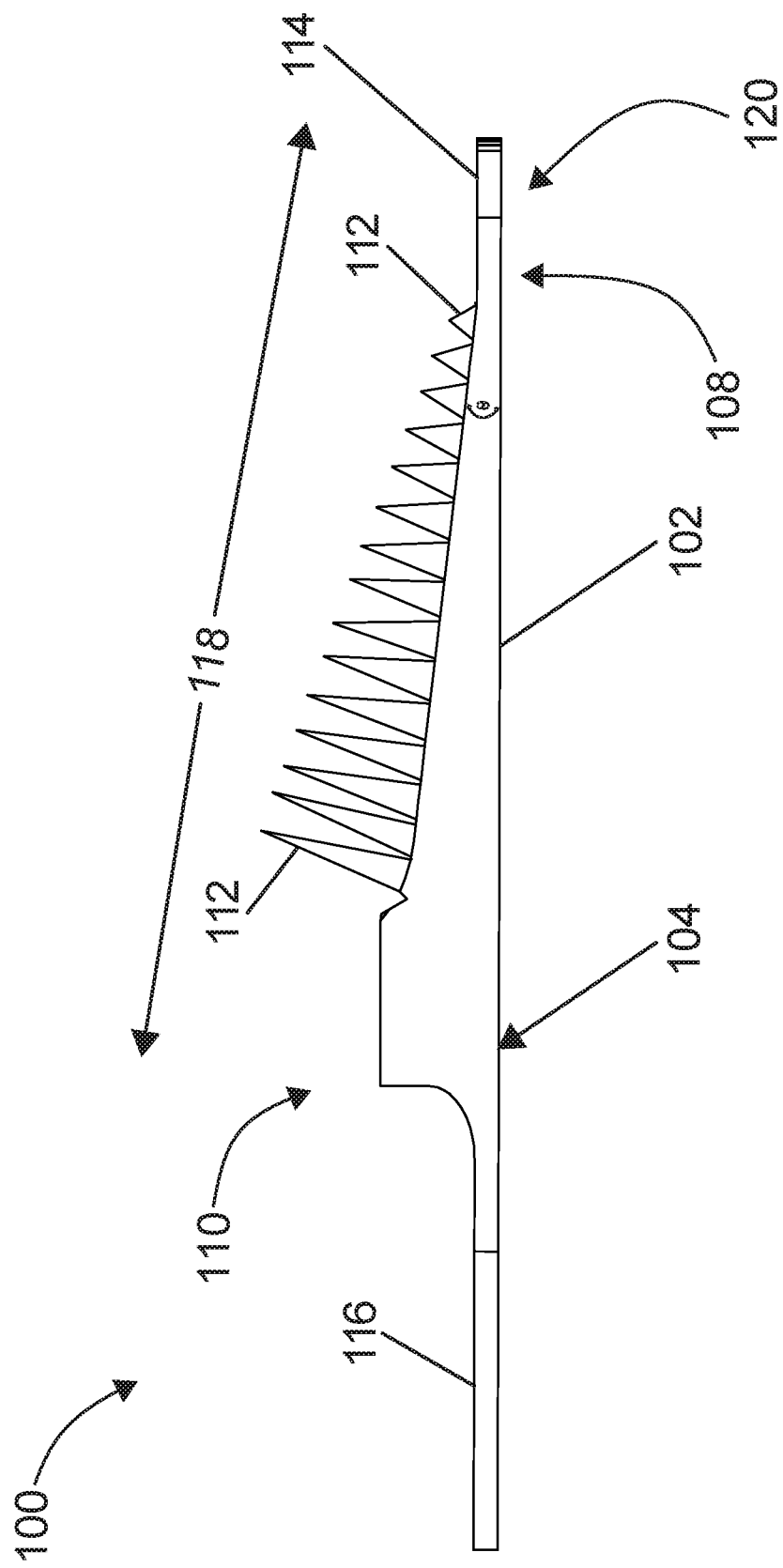
FIG. 1E is a schematic diagram illustrating another side view of the embodiment of a surgical instrument with at least two cutting burrs including different heights.

In various embodiments, the slope 118 includes a grade in the range of about zero degrees (0° or flat) to about fifteen degrees (15°), among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or) 15° is defined between the top surface 106 and the bottom surface 104 beginning at the distal end 108 and extending upward and toward the proximate end 110, as shown in FIGS. 1C, 1D, and 1E. In some embodiments, the slope 118 includes a grade of about seven (7°) degrees (e.g., the angle θ=7° or the angle θ≈7°), among other suitable grades and/or slopes that are possible and contemplated herein.

As illustrated, the top surface 106 includes a set of cutting burrs 112 positioned thereon. The set of cutting burrs 112 may be positioned on the top surface 106 in a patterned configuration or a non-patterned configuration. A patterned configuration (see also surgical instruments 200 and/or 300) may include any suitable pattern of cutting burrs 112 that can assist in and/or facilitate performing an osteotomy and particularly, a wedge-shaped osteotomy. A non-patterned configuration may include any suitable distribution of cutting burrs 112 that can assist in and/or facilitate performing an osteotomy and particularly, a wedge-shaped osteotomy.

A set of cutting burrs 112 may include any suitable quantity of cutting burrs 112 that can facilitate and/or assist the surgical instrument 100 in performing an osteotomy and particularly, a wedge-shaped osteotomy. In various embodiments, the top surface 106 includes a suitable quantity of cutting burrs 112 so that the surgical instrument 100 can perform a wedge-shaped osteotomy in one cut and/or one pass. In various embodiments, the top surface 106 includes a quantity of cutting burrs 112 in the range of about 3 cutting burrs 112 to about 1000 cutting burrs 112, among other ranges of quantities of cutting burrs 112 and/or quantities of cutting burrs 112 that are possible and contemplated herein. In some embodiments, the top surface 106 includes 50 cutting burrs 112, among other quantities of cutting burrs 112 that are possible and contemplated herein.

While the surgical instrument 100 is shown with a top surface 106 including a specific quantity of cutting burrs 112, the various embodiments of the surgical instrument 100 are not limited to the illustrated quantity of cutting burrs 112. That is, various other embodiments of a surgical instrument 100 can include a different quantity of cutting burrs 112 such that the top surface 106 can include a greater quantity of cutting burrs 112 or a smaller quantity of cutting burrs 112 than the illustrated quantity of cutting burrs 112.

In some embodiments, the cutting burrs 112 may be included on the entirety or substantially the entirety of the top surface 106. In other embodiments, the cutting burrs 112 may be included on a portion of the top surface 106 (see FIG. 1D) or at least a portion of the top surface 106.

The portion of the top surface 106 including the cutting burrs 112 may include any suitable sized portion that can produce a wedge-shaped osteotomy. Various embodiments of the surgical instrument 100 may include varying sized portions of the top surface 106 including the cutting burrs 112 so that different sized and/or wedge-shaped osteotomies can be obtained.

A cutting burr 112 may include any suitable shape that can facilitate and/or assist the surgical instrument 100 in performing an osteotomy (e.g., a wedge-shaped osteotomy). In various embodiments, a cutting burr 112 can include a diamond shape, a pointed shape (e.g., a shape that comes to a sharp point), a flame shape, a bullet shape, a cone shape, a tapered shape, or an egg shape, among other suitable shapes that can facilitate cutting bone that are possible and contemplated herein. In additional or alternative embodiments, a cutting burr 112 may be considered the same as or similar to a cutting tooth and/or cutting teeth.

In some embodiments, all of the cutting burrs 112 in the set of cutting burrs 112 on the top surface 106 include the same or substantially the same shape. In alternative embodiments, at least two cutting burrs 112 in the set of cutting burrs 112 on the top surface 106 include different shapes or substantially different shapes. In one non-limiting example, at least one cutting burr 112 includes the diamond shape and at least one cutting burr 112 includes the pointed shape (or other non-diamond shape), among other shapes and/or combinations of shapes that are possible and contemplated herein.

In additional or alternative embodiments, a set of cutting burrs 112 can include at least two subsets of cutting burrs 112 in which a first subset includes two or more cutting burrs 112 including the diamond shape, the flame shape, the pointed shape, the bullet shape, the cone shape, the tapered shape, or the egg shape and at least a second subset includes two or more cutting burrs 112 including a different one of the diamond shape, the flame shape, the pointed shape, the bullet shape, the cone shape, the tapered shape, or the egg shape. In a non-limiting example, a first subset of cutting burrs 112 includes the diamond shape and a second subset of cutting burrs 112 includes the flame shape (or other non-diamond shape), among other shapes and/or combination of shapes that are possible and contemplated herein.

In further additional or alternative embodiments, the first subset of cutting burrs 112 and the second subset of cutting burrs 112 including different shapes include the same quantity of cutting burrs 112. In other embodiments, the first subset of cutting burrs 112 and the second subset of cutting burrs 112 including different shapes include different quantities of cutting burrs 112.

In yet further additional or alternative embodiments, the cutting burrs 112 in the first subset and the cutting burrs 112 in the second subset including different shapes may be distributed on and/or around the top surface 106 of the body 102 in a non-patterned configuration. In other embodiments, the cutting burrs 112 in the first subset of cutting burrs 112 and the cutting burrs 112 in the second subset of cutting burrs 112 including different shapes may be deliberately positioned and/or grouped on and/or around the top surface 106 of the body 102.

In one non-limiting example, the cutting burrs 112 including the diamond shape may be grouped together at a position at or near the distal end 108 (or away from the proximate end 110) or grouped together at a position at or near the proximate end 110 (or away from the distal end 108) and the cutting burrs 112 including an egg shape (or other non-diamond shape) may be positioned opposite the cutting burrs 112 including the diamond shape, among other shapes and/or combinations of shapes that are possible and contemplated herein. In another non-limiting example, a greater quantity of the cutting burrs 112 including the diamond shape may be grouped together at a position at or near the distal end 108 (or away from the proximate end 110) than is grouped together at a position at or near the proximate end 110 (or away from the distal end 108) and the cutting burrs 112 including the non-diamond shape may be positioned opposite the cutting burrs 112 including the diamond shape or vice-versa, among other shapes and/or combinations of shapes that are possible and contemplated herein.

A cutting burr 112 may include any suitable height that can facilitate and/or assist the surgical instrument 100 in performing an osteotomy (e.g., a wedge-shaped osteotomy). In various embodiments, the cutting burrs 112 can include a height in the range of about 0.1 mm to about 30 mm, among other suitable heights that can facilitate cutting bone that are possible and contemplated herein. In some embodiments, the cutting burrs 112 include a height of 0.75 mm.

In some embodiments, all of the cutting burrs 112 in the set of cutting burrs 112 on the top surface 106 can include the same or substantially the same height (see FIG. 1C). In alternative embodiments, at least two cutting burrs 112 in the set of cutting burrs 112 on the top surface 106 include different heights or substantially different heights (see FIG. 1E). In additional or alternative embodiments, a set of cutting burrs 112 can include at least two subsets of cutting burrs 112 in which a first subset includes two or more cutting burrs 112 including a first height that is taller than at least a second subset that includes two or more cutting burrs 112.

In further additional or alternative embodiments, the first subset of cutting burrs 112 and the second subset of cutting burrs 112 including different heights can include the same quantity of cutting burrs 112. In other further additional or alternative embodiments, the first subset of cutting burrs 112 and the second subset of cutting burrs 112 including different heights can include different quantities of cutting burrs 112.

In yet further additional or alternative embodiments, the cutting burrs 112 in the first subset of cutting burrs 112 and the cutting burrs 112 in the second subset of cutting burrs 112 including different heights may be randomly distributed on and/or around the top surface 106 of the body 102. In other embodiments, the cutting burrs 112 in the first subset of cutting burrs 112 and the cutting burrs 112 in the second subset of cutting burrs 112 including different heights may be deliberately positioned and/or grouped on and/or around the top surface 106 of the body 102.

In one non-limiting example, the cutting burrs 112 including the greater height may be grouped together at a position at or near the proximate end 110 (or away from the distal end 108) and the cutting burrs 112 including the smaller height may be positioned at the distal end 108 (or away from the proximate end 110). In another non-limiting example, a greater quantity of the cutting burrs 112 including the smaller height may be grouped together at a position at or near the distal end 108 (or away from the proximate end 110) than is grouped together at a position at or near the proximate end 110 (or away from the distal end 108) and the cutting burrs 112 including the greater height may be positioned opposite the cutting burrs 112 including the smaller height.

As shown, the distal end 108 includes a set of cutting teeth 114 (e.g., a single tooth 114 or multiple teeth 114) positioned thereon. A set of cutting teeth 114 may include any suitable quantity of teeth 114 that can assist in and/or facilitate initiating an osteotomy when oscillated and particularly, a wedge-shaped osteotomy.

In various embodiments, the set of cutting teeth 114 includes a quantity of cutting teeth 114 in the range of one (1) cutting tooth 114 to about 50 cutting teeth 114, among other ranges of quantities and/or quantities of cutting teeth 114 that are possible and contemplated herein. In some embodiments, a set of cutting teeth 114 includes about 8 cutting teeth 114, among other quantities of cutting teeth 114 that are possible and contemplated herein.

In some embodiments, the set of cutting teeth 114 is positioned on the distal end 110 in a straight line or substantially straight line. In other embodiments, the set of cutting teeth 114 is positioned along a curve on the distal end 110 defined by a radius R1.

The radius R1 may be any suitable radius and/or curvature that can assist in and/or facilitate initiating an osteotomy (e.g., a wedge-shaped osteotomy) when oscillated. In various embodiments, the radius R1 is in the range of about 5 mm to about 80 mm, among other ranges of lengths and/or lengths that can define an amount and/or degree of curvature that are possible and contemplated herein. In some embodiments, the radius R1 is about 25 mm, among other lengths that can define an amount and/or degree of curvature that are possible and contemplated herein.

In some embodiments, the set of cutting teeth 114 on the distal end may define a cutting tip 120 that can initiate an osteotomy. Further, the cutting burrs 112 positioned along the single-plane slope 118 may define a cutting slope 118 that can perform the osteotomy to produce a wedge-shaped cut. In various embodiments, the coordination of the cutting tip 120 and the cutting slope 118 can allow the surgical instrument 100 to produce a wedge-shaped osteotomy in a single cut and/or single pass.

As further shown, the proximal end 110 includes an attachment mechanism 116 positioned thereon. The attachment mechanism 116 may include any suitable size dimensions, shape, and/or configuration that enables attachments of the surgical instrument 100 to another surgical instrument (not shown). That is, while the attachment mechanism 116 is shown as including particular relative size dimensions, shapes, and configurations, the various embodiments of the surgical instrument 100 are not limited to the illustrated attachment mechanism 116. That is, other embodiments of the surgical instrument 100 may include one or more different relative size dimension(s), shapes, and/or configurations.

FIGS. 2A through 2E are schematic diagrams illustrating various views of one embodiment of a surgical instrument 200. In various embodiments, the surgical instrument 200 can be utilized to perform a wedge-shaped osteotomy. Further, a wedge-shaped osteotomy can be achieved with a single cut or pass utilizing the surgical instrument 200.

A surgical instrument 200 may be constructed of any suitable material that can cut bone. In various embodiments, the surgical instrument 200 is constructed of a sterilized suitable material that can cut bone. In some embodiments, the surgical instrument 200 includes stainless steel, among other suitable materials that are possible and contemplated herein. In additional or alternative embodiments, the surgical instrument 200 includes surgical grade stainless steel, among other suitable surgical grade materials that are possible and contemplated herein.

At least in the illustrated embodiment, the surgical instrument 200 includes, among other features, a body 202 including at least a bottom surface 204, a top surface 206, a distal end 208, and a proximal end 210, a set of cutting burrs 212 positioned on the body 202 and arranged in multiple rows 222 (e.g., a plurality of rows 222), a set of cutting teeth 214 positioned on the distal end 208, and an attachment mechanism 216 positioned on the proximal end 210. A body 202 may include any suitable dimensions that can perform an osteotomy. In various embodiments, the body 202 includes dimensions that are suitable for performing an osteotomy on a human.

In various embodiments, the body 202 includes a length L2 (see FIG. 2B) in the range of about 15 mm to about 70 mm, among other ranges of length and/or lengths that are possible and contemplated herein. In some embodiments, the body 202 includes a length L2 of about 20 mm, among other lengths that are possible and contemplated herein.

The body 202 further includes a width W3 (see FIG. 2B) at the distal end 208 and a width W4 (see FIG. 2B) at the proximal end 210. In various embodiments, the width W3 is in the range of about 5 mm to about 30 mm, among other ranges of widths and/or widths that are possible and contemplated herein. In some embodiments, the width W3 is about 7.5 mm, among other widths that are possible and contemplated herein. In additional or alternative embodiments, the width W4 is in the range of about 5 mm to about 70 mm, among other ranges of widths and/or widths that are possible and contemplated herein. In some embodiments, the width W4 is about 11 mm, among other widths that are possible and contemplated herein.

In some embodiments, the width W3 and the width W4 are the same width or substantially the same width. In other embodiments, the width W4 is greater than the width W3 such that the proximate end 210 is wider than the distal end 208 or, alternatively, the distal end 208 is narrower than the proximate end 210 (e.g., the width W3 is less than the width W4). That is, in various embodiments, the surgical instrument 200 includes a tapered shape and/or tapers from the distal end 208 to the proximate end 210.

A bottom surface 204 may include any suitable shape and/or profile that can facilitate or assist the surgical instrument 200 in performing an osteotomy (e.g., a wedge-shaped osteotomy). In various embodiments, the bottom surface 204 includes a flat or substantially flat surface, among other profiles and/or planes that are possible and contemplated herein.

A top surface 206 may include any suitable profile upon which a set of cutting burrs 212 can be positioned. In various embodiments, the top surface 206 includes a slope 218 (see FIGS. 2C, 2D, and 2E) that extends upward and/or away from the bottom surface 204. The slope 218 may include any suitable grade (e.g., rise over run) that can facilitate and/or assist the surgical instrument 200 in performing an osteotomy and particularly, a wedge-shaped osteotomy. That is, the top surface 206 and/or surgical instrument 200 may include any suitable grade that can facilitate and/or assist the surgical instrument 200 in performing a wedge-shaped osteotomy in one cut and/or one pass.

Figure 2A:
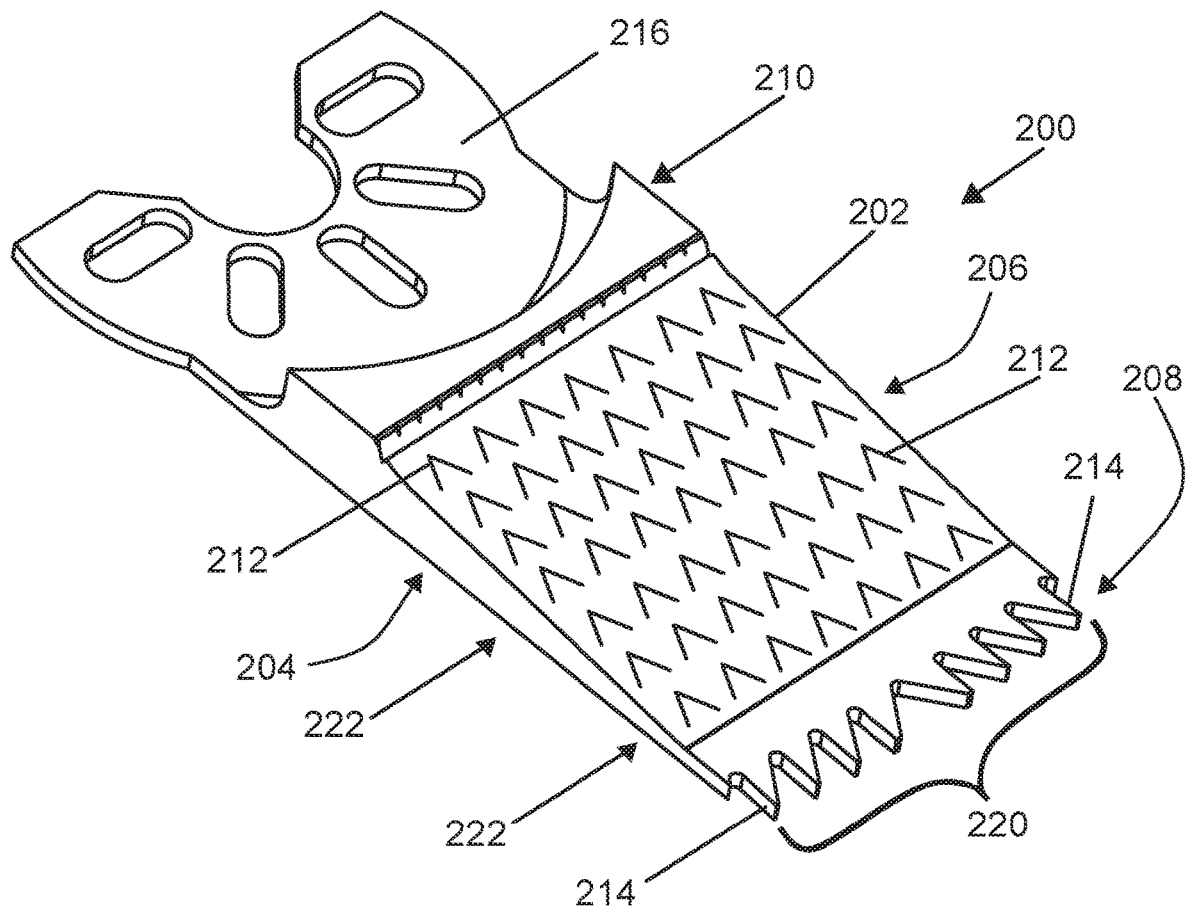
FIG. 2A is a schematic diagram illustrating an overall view of another embodiment of a surgical instrument.
Figure 2B:
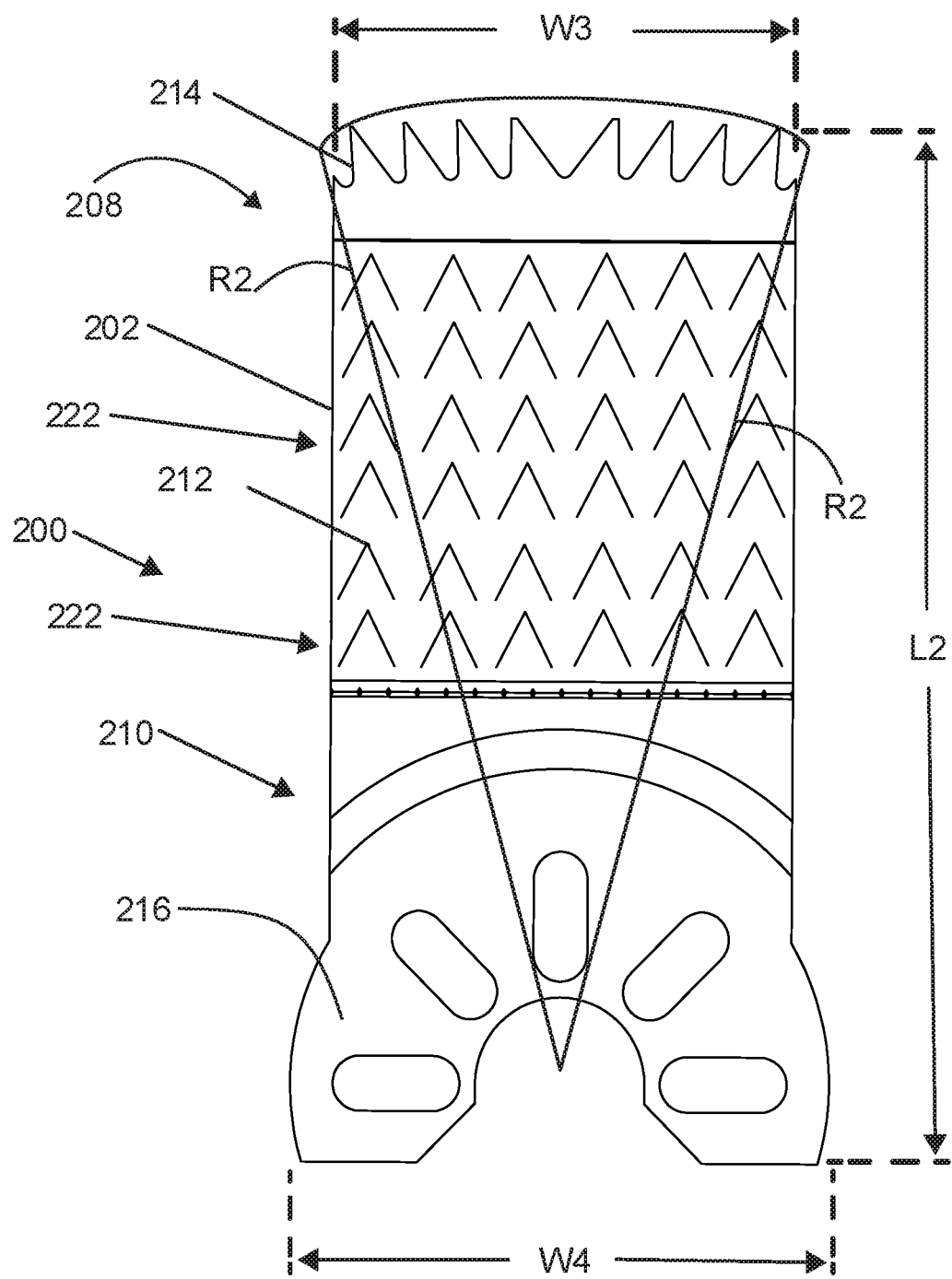
FIG. 2B is a schematic diagram illustrating a top view of the other embodiment of a surgical instrument including rows of cutting burrs on the top surface.
Figure 2C:
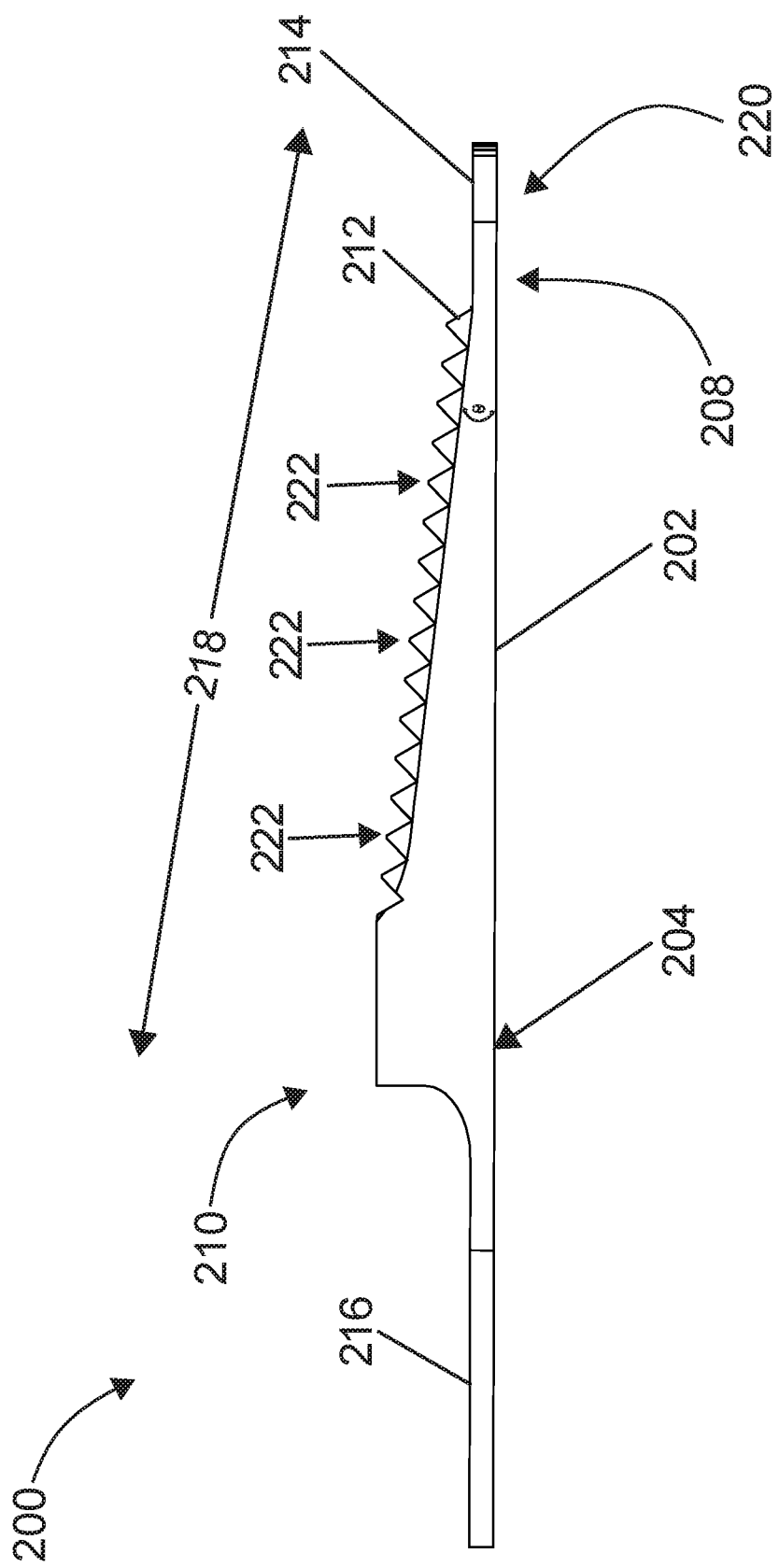
FIG. 2C is a schematic diagram illustrating a side view of the other embodiment of a surgical instrument including cutting burrs with the same height.
Figure 2D:
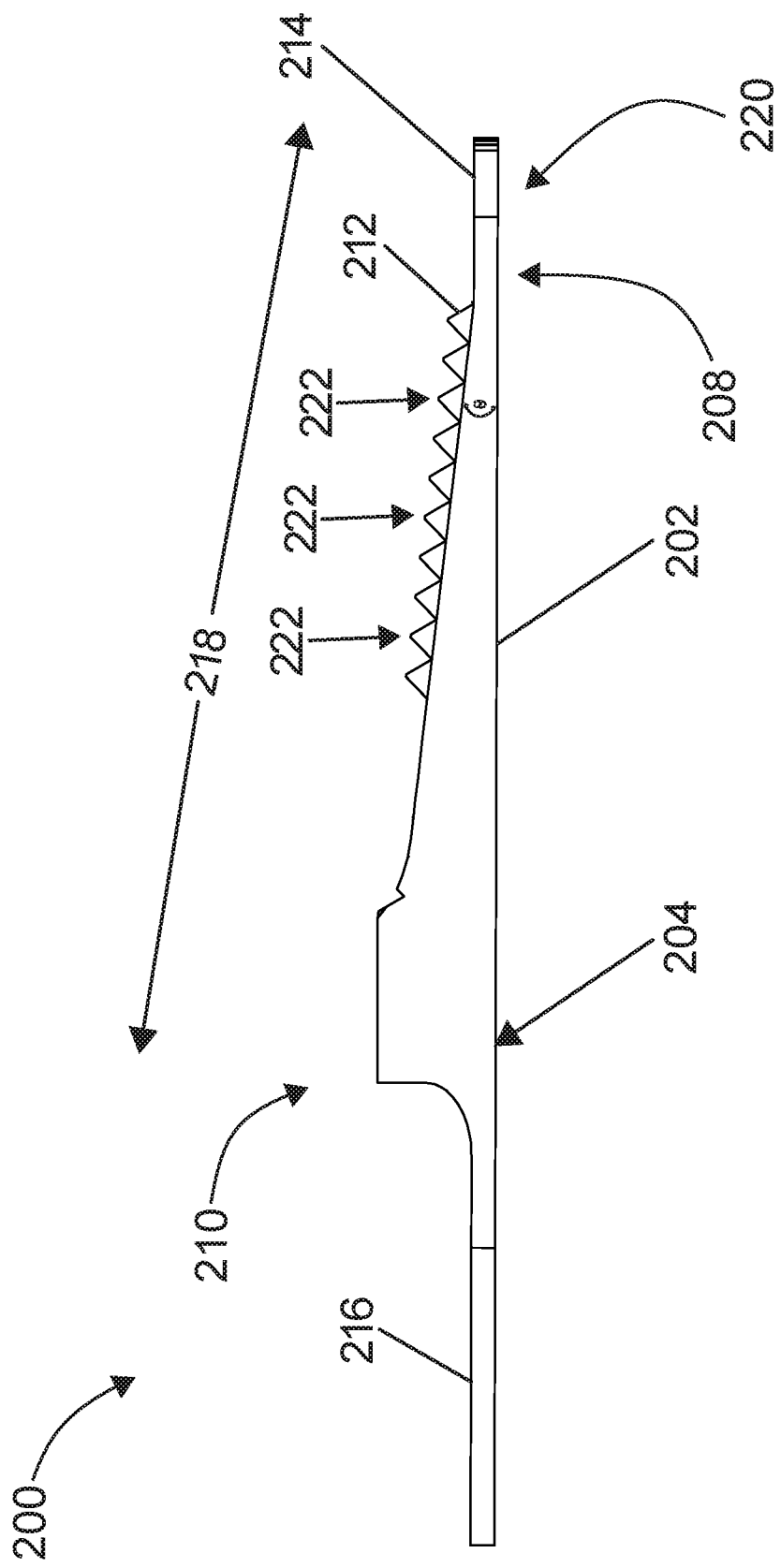
FIG. 2D is a schematic diagram illustrating another top view of the other embodiment of a surgical instrument including rows of cutting burrs on a portion of the top surface.
Figure 2E:
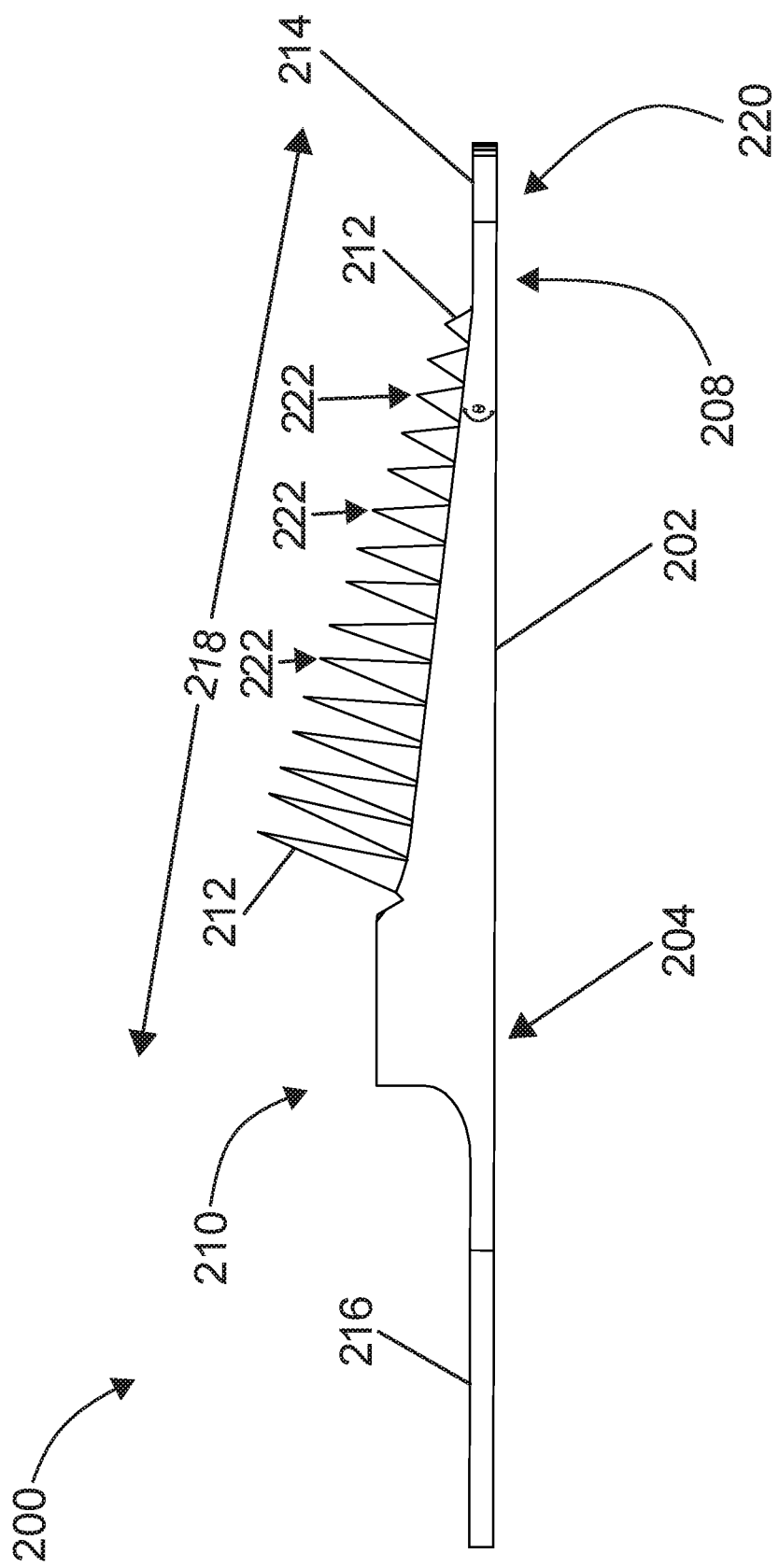
FIG. 2E is a schematic diagram illustrating another side view of the other embodiment of a surgical instrument with at least two cutting burrs including different heights.

In various embodiments, the slope 218 includes a grade in the range of about 0° (or flat) to about 15°, among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 206 and the bottom surface 204 beginning at the distal end 208 and extending upward and toward the proximate end 210, as shown in FIGS. 2C, 2D, and 2E. In some embodiments, the slope 218 includes a grade of about 7° degrees (e.g., the angle θ=7° or the angle θ 7°), among other suitable grades and/or slopes that are possible and contemplated herein.

As illustrated, the top surface 206 includes a set of rows 222 of cutting burrs 212 arranged thereon. The top surface 206 may include any quantity of rows 222 of cutting burrs 212 that can facilitate and/or assist the surgical instrument 200 in performing an osteotomy and particularly, a wedge-shaped osteotomy.

In various embodiments, a set of rows 222 can include a quantity of rows 222 in the range of about two (2) rows 222 of cutting burrs 212 to about 40 rows 222 of cutting burrs 212, among other ranges of quantities and/or quantities that are possible and contemplated herein. In some embodiments, a set of rows 222 includes 12 rows 222 of cutting burrs 212, among other quantities that are possible and contemplated herein.

A row 222 of cutting burrs 212 may include any suitable quantity of cutting burrs 212 that can facilitate and/or assist the surgical instrument 200 in performing an osteotomy and particularly, a wedge-shaped osteotomy. In various embodiments, each row 222 of cutting burrs 212 includes a suitable quantity of cutting burrs 212 so that the surgical instrument 200 can perform a wedge-shaped osteotomy in one cut and/or one pass.

In some embodiments, the top surface 206 includes a quantity of rows 222 of cutting burrs 212 in the range of 1 row 222 of two (2) cutting burrs 212 (e.g., 1×2 cutting burrs 212) to 50 rows 222 of 20 cutting burrs 212 (e.g., 50×20 cutting burrs 212), among other ranges and/or sized matrices that are possible and contemplated herein. In one embodiment, the top surface 206 includes 12 rows 222 of 12 cutting burrs 212 (e.g., 12×12 cutting burrs 212), among other sized matrices that are possible and contemplated herein.

In various embodiments, each row 222 of cutting burrs 212 includes the same quantity of cutting burrs 212. Here, each row 222 of cutting burrs 212 can include a quantity of cutting burrs 212 in the range of about two (2) cutting burrs 212 to about 40 cutting burrs 212, among other ranges of quantities and/or quantities that are possible and contemplated herein. In some embodiments, each row 222 of cutting burrs 212 includes 12 cutting burrs 212, among other quantities that are possible and contemplated herein.

In alternative embodiments, two or more rows 222 of cutting burrs 212 include different quantities of cutting burrs 212. In some embodiments, a first row 222 of cutting burrs 212 can include a quantity of cutting burrs 212 in the range of about two (2) cutting burrs 212 to about 40 cutting burrs 212, among other ranges of quantities and/or quantities that are possible and contemplated herein, and a second row 222 of cutting burrs 212 can include a different quantity of cutting burrs 212 in the range of cutting burrs 212.

While the surgical instrument 200 is shown as including 7 rows 222 of cutting burrs 212, the various embodiments of the surgical instrument 200 are not limited to 7 rows 222 of cutting burrs 212. That is, various other embodiments of a surgical instrument 200 can include a different quantity of rows 222 of cutting burrs 212 such that the top surface 206 can include a greater quantity of rows 222 of cutting burrs 212 than 7 rows 222 of cutting burrs 212 or a smaller quantity of rows 222 of cutting burrs 212 than 7 rows 222 of cutting burrs 212.

In some embodiments, the rows 222 of cutting burrs 212 may be included on the entirety or substantially the entirety of the top surface 206. In other embodiments, the rows 222 of cutting burrs 212 may be included on a portion of the top surface 206 (see FIG. 2D) or at least a portion of the top surface 206.

The portion of the top surface 206 including the rows 222 of cutting burrs 212 may include any suitable sized portion that can produce a wedge-shaped osteotomy. Various embodiments of the surgical instrument 200 may include varying sized portions of the top surface 206 including the rows 222 of cutting burrs 212 so that different sized and/or wedge-shaped osteotomies can be obtained.

A cutting burr 212 may include any suitable shape that can facilitate and/or assist the surgical instrument 200 in performing an osteotomy (e.g., a wedge-shaped osteotomy). In various embodiments, a cutting burr 212 can include a diamond shape, a pointed shape, a flame shape, a bullet shape, a cone shape, a tapered shape, and an egg shape, among other suitable shapes that can facilitate cutting bone that are possible and contemplated herein. In additional or alternative embodiments, a cutting burr 212 may be considered the same as or similar to a cutting tooth and/or cutting teeth.

In some embodiments, all of the cutting burrs 212 in each of the rows 222 of cutting burrs 212 on the top surface 206 include the same or substantially the same shape. In alternative embodiments, at least two rows 222 of cutting burrs 212 on the top surface 206 include different shapes or substantially different shapes. In one non-limiting example, at least one row 222 of cutting burrs 212 includes the diamond shape and at least one row 222 of cutting burrs 212 includes the pointed shape (or other non-diamond shape), among other shapes and/or combinations of shapes that are possible and contemplated herein.

In additional or alternative embodiments, the rows 222 of cutting burrs 212 can be positioned on the top surface 106 in a pattern. The pattern may include any suitable pattern that can assist in and/or facilitate performing an osteotomy. In some embodiments, the pattern may include rows 222 of cutting burrs 212 with different shapes in an alternating pattern to provide alternating rows of cutting burrs 212.

In further additional or alternative embodiments, the rows 222 of cutting burrs 212 different shapes may include the same quantity of cutting burrs 212. In other additional or alternative embodiments, the rows 222 of cutting burrs 212 including different shapes may include different quantities of cutting burrs 212.

In yet further additional or alternative embodiments, the rows 222 of cutting burrs 212 may be deliberately positioned and/or grouped on and/or around the top surface 206 of the body 202. In one non-limiting example, the row(s) 222 of cutting burrs 212 including the diamond shape may be grouped together at a position at or near the distal end 208 (or away from the proximate end 210) or grouped together at a position at or near the proximate end 210 (or away from the distal end 208) and the row(s) 222 of cutting burrs 212 including a non-diamond shape may be positioned opposite the row(s) 222 of cutting burrs 212 including the diamond shape, among other shapes and/or combinations of shapes that are possible and contemplated herein. In another non-limiting example, a greater quantity of rows 222 of cutting burrs 212 including the diamond shape may be grouped together at a position at or near the distal end 208 (or away from the proximate end 210) than is grouped together at a position at or near the proximate end 210 (or away from the distal end 208) and the row(s) 222 of cutting burrs 212 including the non-diamond shape may be positioned opposite the row(s) 222 of cutting burrs 212 including the diamond shape or vice-versa, among other shapes and/or combinations of shapes that are possible and contemplated herein.

A cutting burr 212 may include any suitable height that can facilitate and/or assist the surgical instrument 200 in performing an osteotomy (e.g., a wedge-shaped osteotomy). In various embodiments, the cutting burrs 212 can include a height in the range of about 0.1 mm to about 30 mm, among other suitable heights that can facilitate cutting bone that are possible and contemplated herein. In some embodiments, the cutting burrs 212 include a height of 0.75 mm.

In some embodiments, all of the cutting burrs 212 in the set of cutting burrs 212 on the top surface 206 include the same or substantially the same height (see FIG. 2C). In alternative embodiments, at least two rows 222 of cutting burrs 212 on the top surface 206 include different heights or substantially different heights such that a first row 222 includes a first height that is taller than at least a second row 222.

In various embodiments, the row(s) 222 of cutting burrs 212 including the greater height may be grouped together at a position at or near the proximate end 210 (or away from the distal end 208) and the row(s) 222 of cutting burrs 212 including the smaller height may be positioned at the distal end 208 (or away from the proximate end 210). In additional or alternative embodiments, a greater quantity of rows 222 of cutting burrs 212 including the smaller height may be grouped together at a position at or near the distal end 208 (or away from the proximate end 210) than is grouped together at a position at or near the proximate end 210 (or away from the distal end 208) and the cutting burrs 212 including the greater height may be positioned opposite the cutting burrs 212 including the smaller height.

In further additional or alternative embodiments, the rows 222 of cutting burrs 212 on the top surface 206 each include a different height or a substantially different height. In some embodiments, the rows 222 of cutting burrs 212 include a gradually increasing height from the distal end 108 to the proximal end 110 (e.g., see FIG. 2E).

As shown, the distal end 208 includes a set of cutting teeth 214 (e.g., a single tooth 214 or multiple teeth 214) positioned thereon. A set of cutting teeth 214 may include any suitable quantity of teeth 214 that can assist in and/or facilitate initiating an osteotomy when oscillated and particularly, a wedge-shaped osteotomy.

In various embodiments, the set of cutting teeth 214 includes a quantity of cutting teeth 114 in the range of one cutting tooth 214 to about 50 cutting teeth 214, among other ranges of quantities and/or quantities of cutting teeth 214 that are possible and contemplated herein. In some embodiments, a set of cutting teeth 214 includes about 8 cutting teeth 214, among other quantities of cutting teeth 214 that are possible and contemplated herein.

In some embodiments, the set of cutting teeth 214 is positioned on the distal end 210 in a straight line or substantially straight line. In other embodiments, the set of cutting teeth 214 is positioned along a curve on the distal end 210 defined by a radius R2.

The radius R2 may be any suitable radius and/or curvature that can assist in and/or facilitate initiating an osteotomy (e.g., a wedge-shaped osteotomy) when oscillated. In various embodiments, the radius R2 is in the range of about 5 mm to about 80 mm, among other ranges of lengths and/or lengths that can define an amount and/or degree of curvature that are possible and contemplated herein. In some embodiments, the radius R2 is about 25 mm, among other lengths that can define an amount and/or degree of curvature that are possible and contemplated herein.

In some embodiments, the set of cutting teeth 214 on the distal end may define a cutting tip 220 that can initiate an osteotomy. Further, the cutting burrs 212 positioned along the single-plane slope 218 may define a cutting slope 218 that can perform the osteotomy to produce a wedge-shaped cut. In various embodiments, the coordination of the cutting tip 220 and the cutting slope 218 can allow the surgical instrument 200 to produce a wedge-shaped osteotomy in a single cut and/or single pass.

As further shown, the proximal end 210 includes an attachment mechanism 216 positioned thereon. The attachment mechanism 216 may include any suitable size dimensions, shape, and/or configuration that enables attachments of the surgical instrument 200 to another surgical instrument (not shown). That is, while the attachment mechanism 216 is shown as including particular relative size dimensions, shapes, and configurations, the various embodiments of the surgical instrument 200 are not limited to the illustrated attachment mechanism 216. That is, other embodiments of the surgical instrument 200 may include one or more different relative size dimension(s), shapes, and/or configurations.

FIGS. 3A through 3E are schematic diagrams illustrating various views of one embodiment of a surgical instrument 300. In various embodiments, the surgical instrument 300 can be utilized to perform a wedge-shaped osteotomy. Further, a wedge-shaped osteotomy can be achieved with a single cut or pass utilizing the surgical instrument 300.

A surgical instrument 300 may be constructed of any suitable material that can cut bone. In various embodiments, the surgical instrument 300 is constructed of a sterilized suitable material that can cut bone. In some embodiments, the surgical instrument 300 includes stainless steel, among other suitable materials that are possible and contemplated herein. In additional or alternative embodiments, the surgical instrument 300 includes surgical grade stainless steel, among other suitable surgical grade materials that are possible and contemplated herein.

At least in the illustrated embodiment, the surgical instrument 300 includes, among other features, a body 302 including at least a bottom surface 304, a top surface 306, a distal end 308, and a proximal end 310, a set of cutting burrs 312 positioned on the body 302 and arranged in multiple columns 322 (e.g., a plurality of columns 322), a set of cutting teeth 314 positioned on the distal end 308, and an attachment mechanism 316 positioned on the proximal end 310. A body 302 may include any suitable dimensions that can perform an osteotomy. In various embodiments, the body 302 includes dimensions that are suitable for performing an osteotomy on a human.

In various embodiments, the body 302 includes a length L3 (see FIG. 3B) in the range of about 15 mm to about 70 mm, among other ranges of length and/or lengths that are possible and contemplated herein. In some embodiments, the body 302 includes a length L3 of about 20 mm, among other lengths that are possible and contemplated herein.

The body 302 further includes a width W5 (see FIG. 3B) at the distal end 308 and a width W6 (see FIG. 3B) at the proximal end 310. In various embodiments, the width W5 is in the range of about 5 mm to about 30 mm, among other ranges of widths and/or widths that are possible and contemplated herein. In some embodiments, the width W5 is about 7.5 mm, among other widths that are possible and contemplated herein. In additional or alternative embodiments, the width W6 is in the range of about 5 mm to about 70 mm, among other ranges of widths and/or widths that are possible and contemplated herein. In some embodiments, the width W6 is about 11 mm, among other widths that are possible and contemplated herein.

In some embodiments, the width W5 and the width W6 are the same width or substantially the same width. In other embodiments, the width W6 is greater than the width W5 such that the proximate end 310 is wider than the distal end 308 or, alternatively, the distal end 308 is narrower than the proximate end 310 (e.g., the width W5 is less than the width W6). That is, in various embodiments, the surgical instrument 300 includes a tapered shape and/or tapers from the distal end 308 to the proximate end 310.

A bottom surface 304 may include any suitable shape and/or profile that can facilitate or assist the surgical instrument 300 in performing an osteotomy (e.g., a wedge-shaped osteotomy). In various embodiments, the bottom surface 304 includes a flat or substantially flat surface, among other profiles and/or planes that are possible and contemplated herein.

A top surface 306 may include any suitable profile upon which a set of cutting burrs 312 can be positioned. In various embodiments, the top surface 306 includes a slope 318 (see FIGS. 3C, 3D, and 3E) that extends upward and/or away from the bottom surface 304. The slope 318 may include any suitable grade (e.g., rise over run) that can facilitate and/or assist the surgical instrument 300 in performing an osteotomy and particularly, a wedge-shaped osteotomy. That is, the top surface 306 and/or surgical instrument 300 may include any suitable grade that can facilitate and/or assist the surgical instrument 300 in performing a wedge-shaped osteotomy in one cut and/or one pass.

Figure 3A:
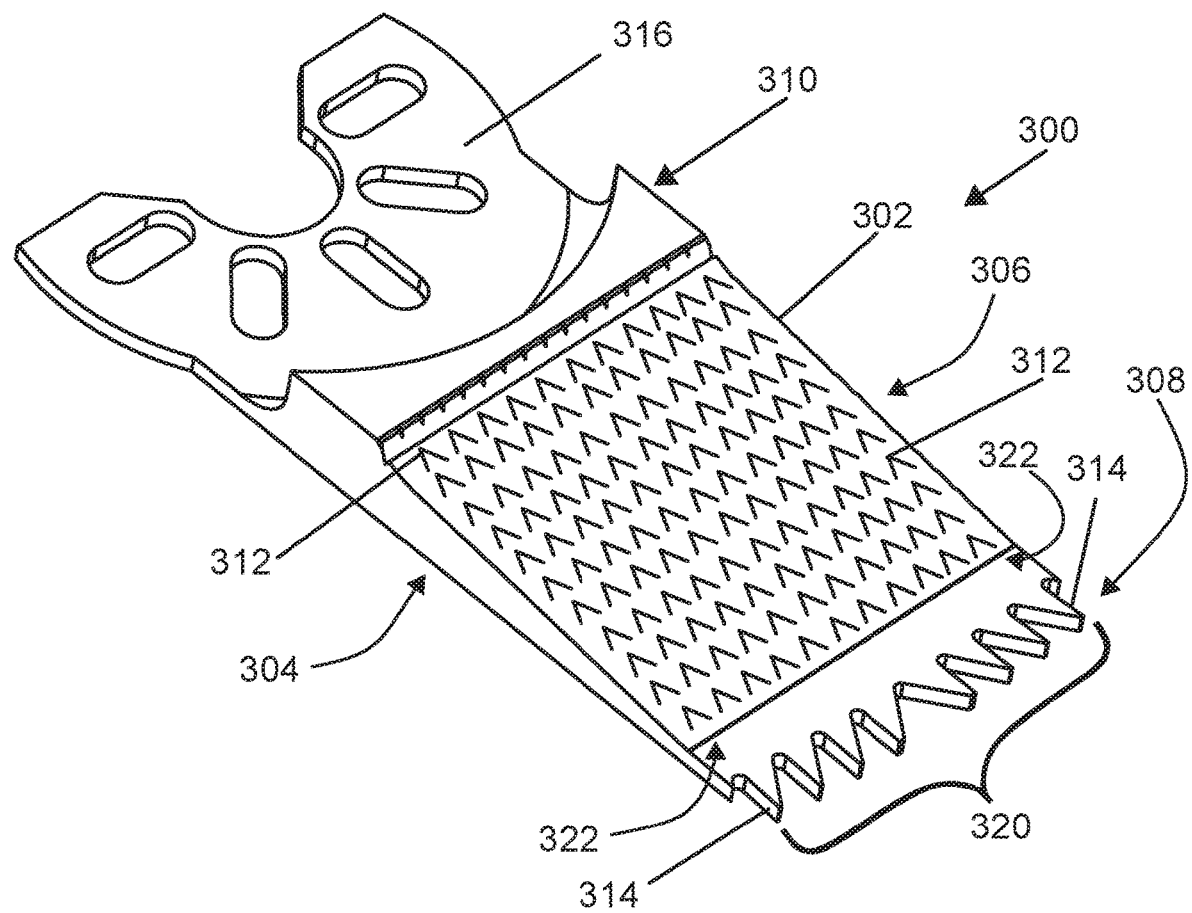
FIG. 3A is a schematic diagram illustrating an overall view of another embodiment of a surgical instrument.
Figure 3B:
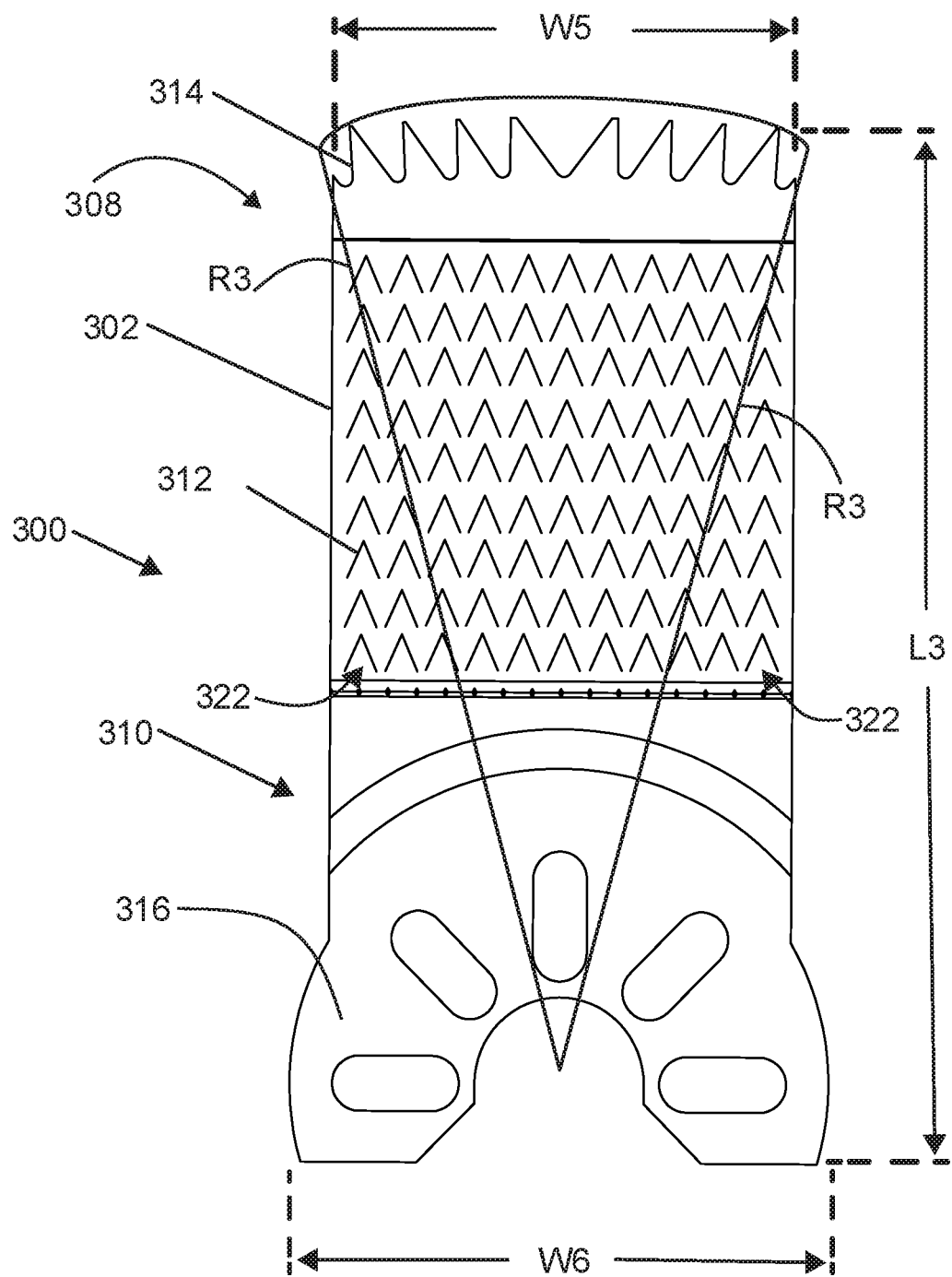
FIG. 3B is a schematic diagram illustrating a top view of the other embodiment of a surgical instrument including rows of cutting burrs on the top surface.
Figure 3C:
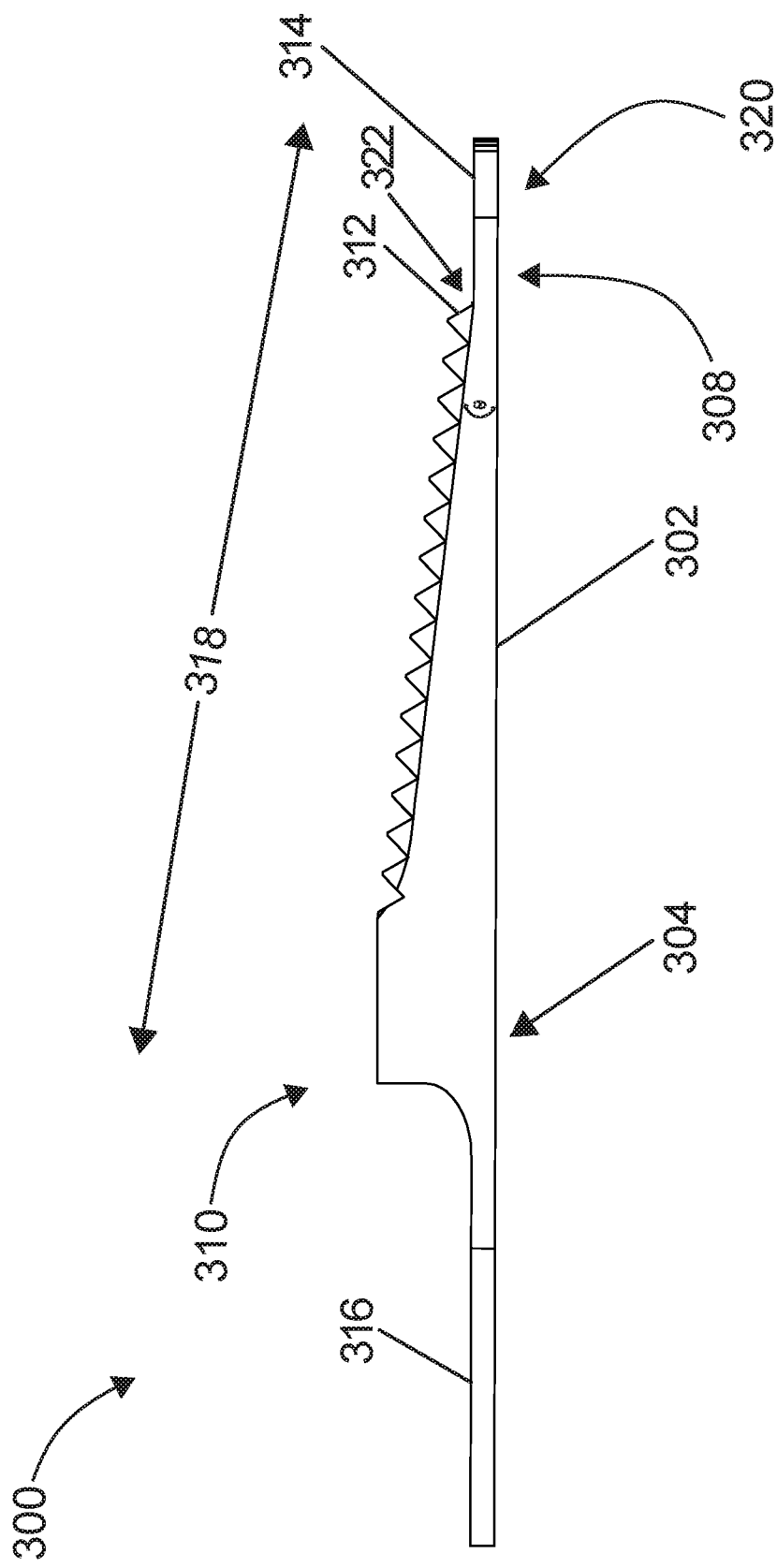
FIG. 3C is a schematic diagram illustrating a side view of the other embodiment of a surgical instrument including cutting burrs with the same height.
Figure 3D:
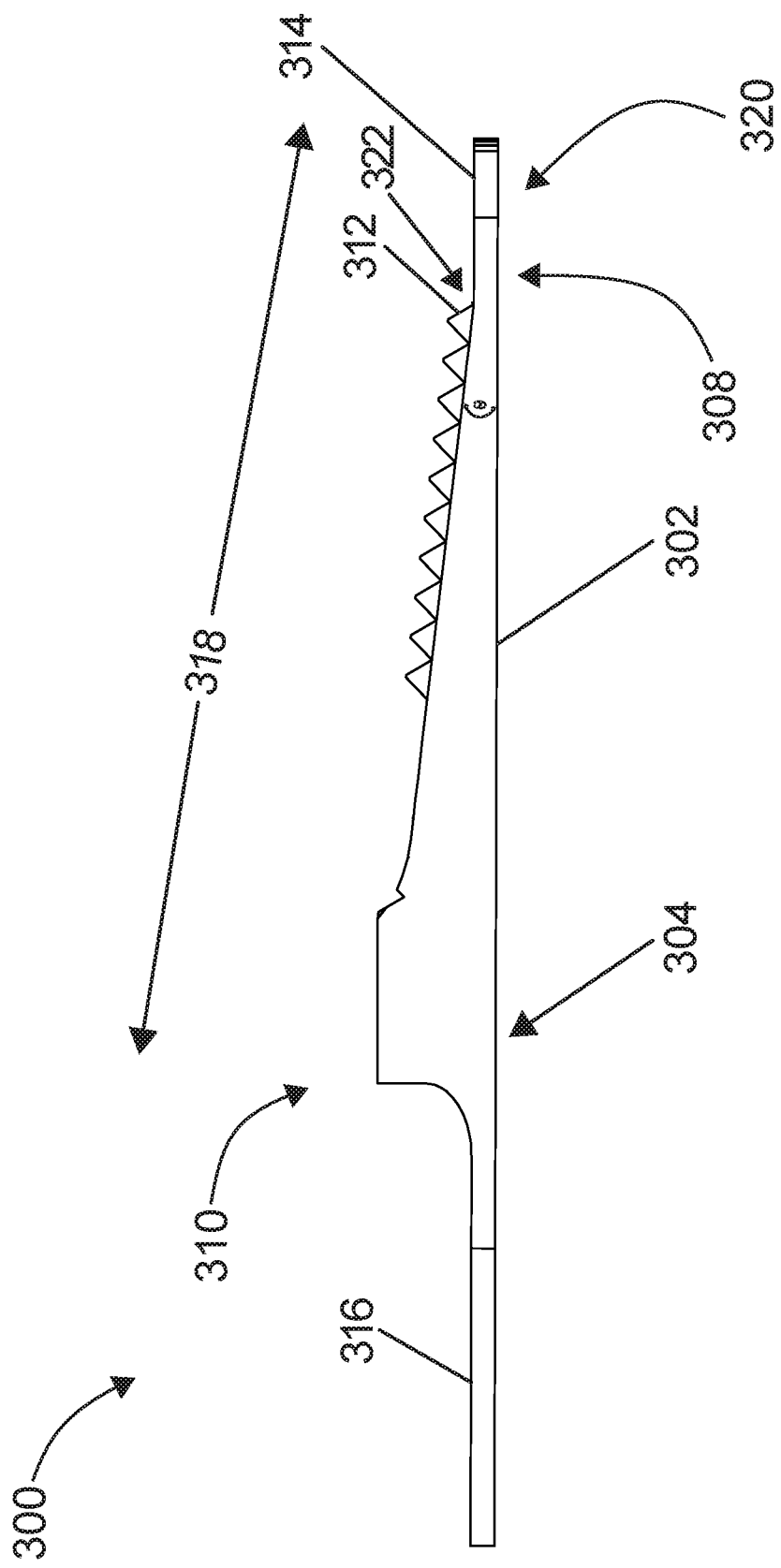
FIG. 3D is a schematic diagram illustrating another top view of the other embodiment of a surgical instrument including rows of cutting burrs on a portion of the top surface.
Figure 3E:
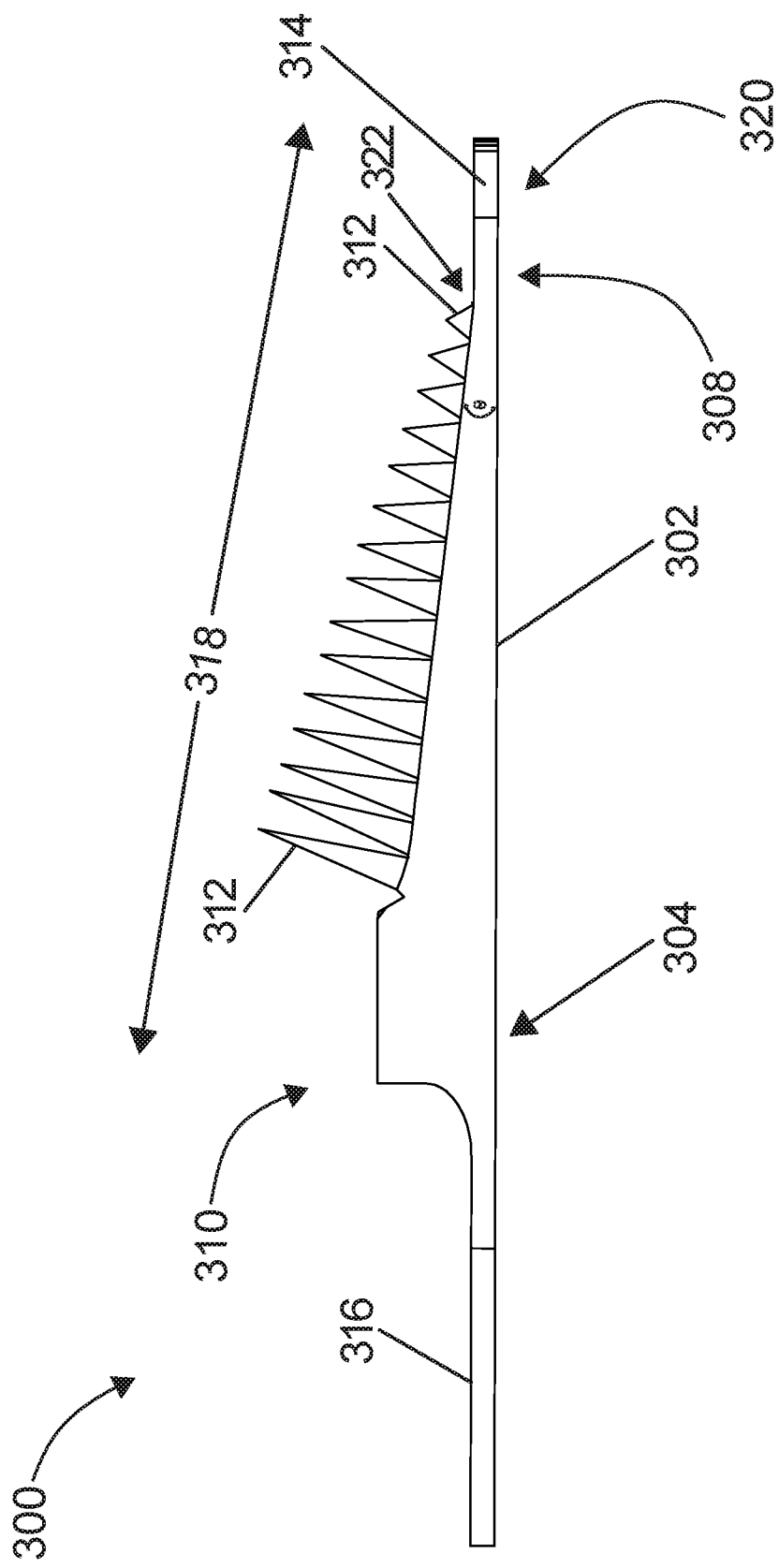
FIG. 3E is a schematic diagram illustrating another side view of the other embodiment of a surgical instrument with at least two cutting burrs including different heights.

In various embodiments, the slope 318 includes a grade in the range of about 0° (or flat) to about 15°, among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 306 and the bottom surface 304 beginning at the distal end 308 and extending upward and toward the proximate end 310, as shown in FIGS. 3C, 3D, and 3E. In some embodiments, the slope 318 includes a grade of about 7° degrees (e.g., the angle θ=7° or the angle θ 7°), among other suitable grades and/or slopes that are possible and contemplated herein.

As illustrated, the top surface 306 includes a set of columns 322 of cutting burrs 312 arranged thereon. The top surface 306 may include any quantity of columns 322 of cutting burrs 312 that can facilitate and/or assist the surgical instrument 300 in performing an osteotomy and particularly, a wedge-shaped osteotomy. In various embodiments, a set of columns 322 can include a quantity of columns 322 in the range of about two (2) columns 322 of cutting burrs 312 to about 40 columns 322 of cutting burrs 312, among other ranges of quantities and/or quantities that are possible and contemplated herein. In some embodiments, a set of columns 322 includes 12 columns 322 of cutting burrs 312, among other quantities that are possible and contemplated herein.

A column 322 of cutting burrs 312 may include any suitable quantity of cutting burrs 312 that can facilitate and/or assist the surgical instrument 300 in performing an osteotomy and particularly, a wedge-shaped osteotomy. In various embodiments, each column 322 of cutting burrs 312 includes a suitable quantity of cutting burrs 312 so that the surgical instrument 300 can perform a wedge-shaped osteotomy in one cut and/or one pass.

In some embodiments, the top surface 306 includes a quantity of columns 322 of cutting burrs 312 in the range of 1 column 322 of two (2) cutting burrs 312 (e.g., 1×2 cutting burrs 312) to 20 columns 322 of 50 cutting burrs 312 (e.g., 20×50 cutting burrs 312), among other ranges and/or sized matrices that are possible and contemplated herein. In one embodiment, the top surface 306 includes 12 columns 322 of 12 cutting burrs 312 (e.g., 12×12 cutting burrs 312), among other sized matrices that are possible and contemplated herein.

In various embodiments, each column 322 of cutting burrs 312 includes the same quantity of cutting burrs 312. Here, each column 322 of cutting burrs 312 can include a quantity of cutting burrs 312 in the range of about 3 cutting burrs 312 to about 40 cutting burrs 312, among other ranges of quantities and/or quantities that are possible and contemplated herein. In some embodiments, each column 322 of cutting burrs 312 includes 11 cutting burrs 312, among other quantities that are possible and contemplated herein.

In alternative embodiments, two or more columns 322 of cutting burrs 312 include different quantities of cutting burrs 312. In some embodiments, a first column 322 of cutting burrs 312 can include a quantity of cutting burrs 312 in the range of about 3 cutting burrs 312 to about 40 cutting burrs 312, among other ranges of quantities and/or quantities that are possible and contemplated herein, and a second column 322 of cutting burrs 312 can include a different quantity of cutting burrs 312 in the range of cutting burrs 312.

While the surgical instrument 300 is shown as including 11 columns 322 of cutting burrs 312, the various embodiments of the surgical instrument 300 are not limited to 11 columns 322 of cutting burrs 312. That is, various other embodiments of a surgical instrument 300 can include a different quantity of columns 322 of cutting burrs 312 such that the top surface 306 can include a greater quantity of columns 322 of cutting burrs 312 than 11 columns 322 of cutting burrs 312 or a smaller quantity of columns 322 of cutting burrs 312 than 11 columns 322 of cutting burrs 312.

In some embodiments, the columns 322 of cutting burrs 312 may be included on the entirety or substantially the entirety of the top surface 306. In other embodiments, the columns 322 of cutting burrs 312 may be included on a portion of the top surface 306 (see FIG. 3D) or at least a portion of the top surface 306.

The portion of the top surface 306 including the columns 322 of cutting burrs 312 may include any suitable sized portion that can produce a wedge-shaped osteotomy. Various embodiments of the surgical instrument 300 may include varying sized portions of the top surface 306 including the columns 322 of cutting burrs 312 so that different sized and/or wedge-shaped osteotomies can be obtained.

A cutting burr 312 may include any suitable shape that can facilitate and/or assist the surgical instrument 300 in performing an osteotomy (e.g., a wedge-shaped osteotomy). In various embodiments, a cutting burr 312 can include a diamond shape, a pointed shape, a flame shape, a bullet shape, a cone shape, a tapered shape, and an egg shape, among other suitable shapes that can facilitate cutting bone that are possible and contemplated herein. In additional or alternative embodiments, a cutting burr 312 may be considered the same as or similar to a cutting tooth and/or cutting teeth.

In some embodiments, all of the cutting burrs 312 in each of the columns 322 of cutting burrs 312 on the top surface 306 include the same or substantially the same shape. In alternative embodiments, at least two columns 322 of cutting burrs 312 on the top surface 306 include different shapes or substantially different shapes. In one non-limiting example, at least one column 322 of cutting burrs 312 includes the diamond shape and at least one column 322 of cutting burrs 312 includes the pointed shape (or other non-diamond shape), among other shapes and/or combinations of shapes that are possible and contemplated herein.

In additional or alternative embodiments, the columns 322 of cutting burrs 312 can be positioned on the top surface 106 in a pattern. The pattern may include any suitable pattern that can assist in and/or facilitate performing an osteotomy. In some embodiments, the pattern may include columns 322 of cutting burrs 312 with different shapes in an alternating pattern to provide alternating columns of cutting burrs 312.

In further additional or alternative embodiments, the columns 322 of cutting burrs 312 different shapes may include the same quantity of cutting burrs 312. In other additional or alternative embodiments, the columns 322 of cutting burrs 312 including different shapes may include different quantities of cutting burrs 312.

A cutting burr 312 may include any suitable height that can facilitate and/or assist the surgical instrument 300 in performing an osteotomy (e.g., a wedge-shaped osteotomy). In various embodiments, the cutting burrs 312 can include a height in the range of about 0.1 mm to about 30 mm, among other suitable heights that can facilitate cutting bone that are possible and contemplated herein. In some embodiments, the cutting burrs 312 include a height of 0.75 mm.

In some embodiments, all of the cutting burrs 312 in the set of cutting burrs 312 on the top surface 306 include the same or substantially the same height (see FIG. 3C). In alternative embodiments, at least one column 322 on the top surface 306 includes cutting burrs 312 with different heights or substantially different heights such that a first cutting burr 312 includes a height that is taller than at least a second cutting burr 312 in the column 322.

In various embodiments, the cutting burr(s) 312 including the greater height may be located at a position in its/their respective column 322 that at or near the proximate end 310 (or away from the distal end 308) and the cutting burr(s) 312 including the smaller height may be positioned at the distal end 308 (or away from the proximate end 310). In some embodiments, the columns 322 of cutting burrs 312 include a set of cutting burrs 312 therein that include a gradually increasing height from the distal end 108 to the proximal end 110 (e.g., see FIG. 3E).

As shown, the distal end 308 includes a set of cutting teeth 314 (e.g., a single tooth 314 or multiple teeth 314) positioned thereon. A set of cutting teeth 314 may include any suitable quantity of teeth 314 that can assist in and/or facilitate initiating an osteotomy when oscillated and particularly, a wedge-shaped osteotomy.

In various embodiments, the set of cutting teeth 314 includes a quantity of cutting teeth 314 in the range of one cutting tooth 314 to about 50 cutting teeth 314, among other ranges of quantities and/or quantities of cutting teeth 314 that are possible and contemplated herein. In some embodiments, a set of cutting teeth 314 includes about 8 cutting teeth 314, among other quantities of cutting teeth 314 that are possible and contemplated herein.

In some embodiments, the set of cutting teeth 314 is positioned on the distal end 310 in a straight line or substantially straight line. In other embodiments, the set of cutting teeth 314 is positioned along a curve on the distal end 310 defined by a radius R3.

The radius R3 may be any suitable radius and/or curvature that can assist in and/or facilitate initiating an osteotomy (e.g., a wedge-shaped osteotomy) when oscillated. In various embodiments, the radius R3 is in the range of about 5 mm to about 80 mm, among other ranges of lengths and/or lengths that can define an amount and/or degree of curvature that are possible and contemplated herein. In some embodiments, the radius R3 is about 25 mm, among other lengths that can define an amount and/or degree of curvature that are possible and contemplated herein.

In some embodiments, the set of cutting teeth 314 on the distal end may define a cutting tip 320 that can initiate an osteotomy. Further, the cutting burrs 312 positioned along the single-plane slope 318 may define a cutting slope 318 that can perform the osteotomy to produce a wedge-shaped cut. In various embodiments, the coordination of the cutting tip 320 and the cutting slope 318 can allow the surgical instrument 300 to produce a wedge-shaped osteotomy in a single cut and/or single pass.

As further shown, the proximal end 310 includes an attachment mechanism 316 positioned thereon. The attachment mechanism 316 may include any suitable size dimensions, shape, and/or configuration that enables attachments of the surgical instrument 300 to another surgical instrument (not shown). That is, while the attachment mechanism 316 is shown as including particular relative size dimensions, shapes, and configurations, the various embodiments of the surgical instrument 300 are not limited to the illustrated attachment mechanism 316. That is, other embodiments of the surgical instrument 300 may include one or more different relative size dimension(s), shapes, and/or configurations.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

The invention claimed is:

1. A surgical instrument, comprising:
a body comprising a distal end, a proximal end, a bottom surface, and a top surface including a slope extending upward and along a single plane from the distal end to the proximal end;
a plurality of cutting burrs positioned on the top surface and extending along at least a portion of the slope from the distal end to the proximal end; and
a set of teeth positioned along a radius on the distal end, wherein:
the plurality of cutting burrs are oriented vertically with respect to the slope of the top surface, and
the proximal end includes a first horizontal width that is greater than a second horizontal width for the distal end such that the body tapers from the distal end to the proximal end.

2. The surgical instrument of claim 1, wherein the slope defines an angle in the range of 1 degree and 15 degrees between the top surface and the bottom surface.

3. The surgical instrument of claim 1, wherein:
each cutting burr in the plurality of cutting burrs comprises a shape; and
the shape comprises one of a diamond shape, a pointed shape, a cone shape, and a tapered shape.

4. The surgical instrument of claim 1, wherein:
each cutting burr in the plurality of cutting burrs comprises a shape; and
at least two cutting burrs in the plurality of cutting burrs comprise different shapes.

5. The surgical instrument of claim 4, wherein:
a first cutting burr in the plurality of cutting burrs includes the one of a diamond shape, a pointed shape, a cone shape, and a tapered shape; and
a second cutting burr in the plurality of cutting burrs includes a different one of the diamond shape, the pointed shape, the bullet shape, the cone shape, and the tapered shape.

6. The surgical instrument of claim 5, wherein:
two or more first cutting burrs in the plurality of cutting burrs includes the one of the diamond shape, the pointed shape, the cone shape, and the tapered shape; and
two or more second cutting burrs in the plurality of cutting burrs includes the different one of the diamond shape, the pointed shape, the cone shape, and the tapered shape.

7. The surgical instrument of claim 1, wherein at least two cutting burrs include different sizes.

8. The surgical instrument of claim 7, wherein:
a first cutting burr includes a first height that is greater than a second height for a second cutting burr; and
the first cutting burr is located on the top surface closer to the proximal end than the second cutting burr.

9. A surgical instrument, comprising:
a body comprising a distal end, a proximal end, a bottom surface, and a top surface including a slope extending upward and along a single plane from the distal end to the proximal end;
a plurality of rows of cutting burrs positioned on the top surface and extending along at least a portion of the slope from the distal end to the proximal end; and
a set of teeth positioned along a radius on the distal end, wherein:
the plurality of rows of cutting burrs are oriented vertically with respect to the slope of the top surface, and
the proximal end includes a first horizontal width that is greater than a second horizontal width for the distal end such that the body tapers from the distal end to the proximal end.

10. The surgical instrument of claim 9, wherein the slope defines an angle in the range of 1 degree and 15 degrees between the top surface and the bottom surface.

11. The surgical instrument of claim 9, wherein each cutting burr comprises one of a diamond shape, a pointed shape, a cone shape, and a tapered shape.

12. The surgical instrument of claim 11, wherein at least two cutting burrs comprise different shapes.

13. The surgical instrument of claim 12, wherein:
one or more first cutting burrs includes one of a diamond shape, a pointed shape, a cone shape, and a tapered shape; and
one or more second cutting burrs includes a different one of the diamond shape, the pointed shape, the cone shape, and the tapered shape.

14. The surgical instrument of claim 9, wherein at least two cutting burrs include different sizes.

15. The surgical instrument of claim 14, wherein:
a first cutting burr includes a first height that is greater than a second height for a second cutting burr; and
the first cutting burr is located on the top surface closer to the proximal end than the second cutting burr.

16. The surgical instrument of claim 9, wherein:
a first row of cutting burrs includes a first plurality of cutting burrs;
a second row of cutting burrs includes a second plurality of cutting burrs; and
cutting burrs in the first row of cutting burrs and cutting burrs in the second row of cutting burrs include different sizes.

17. The surgical instrument of claim 16, wherein:
the cutting burrs in the first row of cutting burrs include a first height that is greater than a second height for the cutting burrs in the second row of cutting burrs; and
the first row of cutting burrs is located on the top surface closer to the proximal end than the second row of cutting burrs.

18. The surgical instrument of claim 9, wherein the plurality of row of cutting burrs are oriented perpendicular with respect to the slope of the top surface.

19. A surgical instrument, comprising:
a body comprising a distal end, a proximal end, a bottom surface, and a top surface including a slope extending upward and along a single plane from the distal end to the proximal end;
a plurality of cutting burrs positioned on the top surface and extending along at least a portion of the slope from the distal end to the proximal end; and
a set of teeth positioned along a radius on the distal end, wherein:
the plurality of cutting burrs are oriented perpendicular with respect to the slope of the top surface, and
the proximal end includes a first horizontal width that is greater than a second horizontal width for the distal end such that the body tapers from the distal end to the proximal end.

20. The surgical instrument of claim 19, wherein the slope defines an angle in the range of 1 degree and 15 degrees between the top surface and the bottom surface.

* * * * *